United States Patent
Wang et al.

(10) Patent No.: US 11,512,074 B2
(45) Date of Patent: Nov. 29, 2022

(54) SUBSTITUTED DIAMINO HETEROCYCLIC CARBOXAMIDE COMPOUND AND A COMPOSITION CONTAINING THE COMPOUND AND USE THEREOF

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 59 days.

(21) Appl. No.: 16/971,128

(22) PCT Filed: Mar. 28, 2019

(86) PCT No.: PCT/CN2019/080011
§ 371 (c)(1),
(2) Date: Aug. 19, 2020

(87) PCT Pub. No.: WO2019/184966
PCT Pub. Date: Oct. 3, 2019

(65) Prior Publication Data
US 2021/0094939 A1    Apr. 1, 2021

(30) Foreign Application Priority Data

Mar. 28, 2018   (CN) .......................... 201810262188.5

(51) Int. Cl.
| C07D 405/14 | (2006.01) |
| A61P 35/00  | (2006.01) |
| A61P 35/02  | (2006.01) |
| A61K 31/497 | (2006.01) |

(52) U.S. Cl.
CPC ............ *C07D 405/14* (2013.01); *A61P 35/02* (2018.01); *C07B 2200/05* (2013.01)

(58) Field of Classification Search
CPC ........ C07D 405/14; A61P 35/02; A61P 35/00; C07B 2200/05; A61K 31/497
See application file for complete search history.

(56) References Cited

U.S. PATENT DOCUMENTS

| 2008/0299215 A1 | 12/2008 | Czarnik |
| 2009/0076025 A1 | 3/2009  | Czarnik |

FOREIGN PATENT DOCUMENTS

| CN | 106083821 A      | 11/2006 |
| CN | 102421761 A      | 4/2012  |
| CN | 201980014848.0   | 6/2022  |
| JP | 2014-005206 A    | 1/2014  |
| WO | WO 2010/128659 A1| 11/2010 |
| WO | WO 2015/125785 A1| 8/2015  |

OTHER PUBLICATIONS

Buteau, K. C., "Deuterated Drugs: Unexpectedly Nonobvious?", Journal of High Technology Law 2009 10(1):22-74).*
Gant, T.G., "Using deuterium in drug discovery: leaving the label in the drug." Journal of medicinal chemistry 57.9 (2014): 3595-3611.*
Xu, G., "Design, synthesis, and biological evaluation of deuterated C-aryl glycoside as a potent and long-acting renal sodium-dependent glucose cotransporter 2 inhibitor for the treatment of type 2 diabetes." Journal of Medicinal Chemistry 57.4 (2014): 1236-1251.*
Di Gion, P., "Clinical pharmacokinetics of tyrosine kinase inhibitors." Clinical pharmacokinetics 50.9 (2011): 551-603.*
PCT/CN2019/080011, Jun. 27, 2019, International Search Report and Written Opinion and English translation thereof.
PCT/CN2019/080011, Oct. 8, 2020, International Preliminary Report on Patentability and English translation thereof.
International Search Report and Written Opinion for Application No. PCT/CN2019/080011, dated Jun. 27, 2019.

(Continued)

*Primary Examiner* — John M Mauro
(74) *Attorney, Agent, or Firm* — Wolf, Greenfield & Sacks, P.C.

(57) ABSTRACT

A substituted amino heterocyclic carboxamide compound as represent by formula (Φ), or a pharmaceutically acceptable salt, a prodrug, a hydrate or a solvent compound, a crystal form, a stereoisomer or an isotopic variant of the compound, and a pharmaceutical composition thereof, and the use thereof as an FLT3/AXL kinase inhibitor for treating acute myelocytic leukemia.

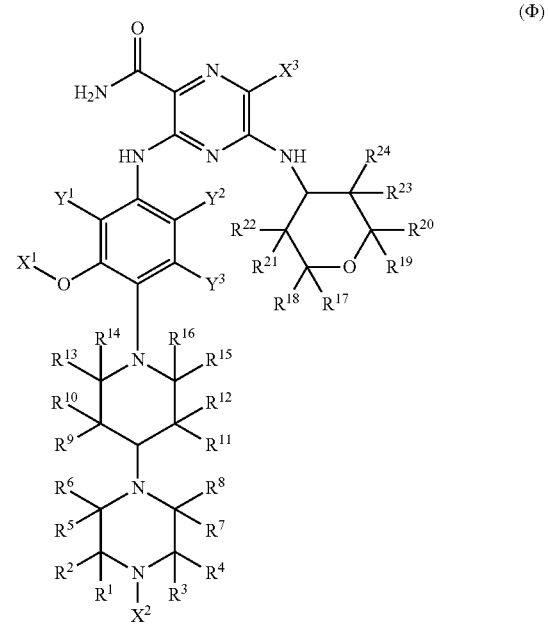

(Φ)

13 Claims, No Drawings

(56) References Cited

OTHER PUBLICATIONS

International Preliminary Report on Patentability for Application No. PCT/CN2019/080011, dated Oct. 8, 2020.
Mori et al., Gilteritinib, a FLT3/AXL inhibitor, shows antileukemic activity in mouse models of FLT3 mutated acute myeloid leukemia. Invest New Drugs. Oct. 2017;35(5):556-565. doi: 10.1007/s10637-017-0470-z. Epub May 17, 2017.
Zhang et al., Development of Deuterated Drugs: Past, Present and Future. Progress in Pharmaceutical Sciences. Dec. 31, 2017; 41(12):902-918.
Foster, Deuterium isotope effects in the metabolism of drugs and xenobiotics implications for drug design. Advances in Drug Research. 1985; 14: 1-40.
Declaration under 37 CFR § 1.132 for Vinita Uttamsingh, dated Feb. 1, 2012. 3 pages.
Harbeson et al., Deuterium in Drug Discovery and Development. Ann Rep Med Chem. 2011;46:403-417.
Shao et al., Derivatives of tramadol for increased duration of effect. Bioorg Med Chem Lett. 2006;16:691-694.
Chinese Office Action for Application No. 201980014848.0, dated Jun. 14, 2022.
Jiang et al., Application of deuteration in drug research. Qilu Pharmaceutical Affairs. 2010;29(11):682-4.

* cited by examiner

SUBSTITUTED DIAMINO HETEROCYCLIC CARBOXAMIDE COMPOUND AND A COMPOSITION CONTAINING THE COMPOUND AND USE THEREOF

CROSS REFERENCE TO RELATED APPLICATIONS

The present application is a national application of PCT/CN2019/080011 filed on Mar. 28, 2019, which claims the priority of the Chinese Patent Application No. 201810262188.5 filed on Mar. 28, 2018. The Chinese Patent Application No. 201810262188.5 is incorporated herein by reference as part of the disclosure of the present application.

FIELD OF THE INVENTION

The present disclosure relates to the field of pharmaceutical technology, particularly relates to a substituted diamino heterocyclic carboxamide compound, a composition comprising the same and use thereof. More specifically, the present disclosure relates to some deuterated 6-ethyl-3-((3-methoxy-4-(4-(4-methylpiperazin-1-yl)piperidin-1-yl)phenyl)amino)-5-((tetrahydro-2H-pyra n-4-yl)amino)pyrazine-2-carboxamides. These deuterated compounds are demonstrated as inhibitors of AXL and FLT3 protein tyrosine kinase, which can be used in the treatment of diseases mediated by AXL and/or FLT3, and have better pharmacokinetic and pharmacodynamic properties.

BACKGROUND OF THE INVENTION

Acute Myeloid Leukemia (Acute Myelocytic Leukemia, AML) is a disease caused by the malignant proliferation of hematopoietic progenitor cells of bone marrow. The poorly differentiated progenitor cells lose their normal functions which disrupts the normal hematopoietic process, leading to infections, bleeding and multiple organ dysfunctions. The overall incidence of AML is 3.4/100,000, and the median of patients' age is 67. The onset of disease occurs before the age of 65 for more than half of the patients. The prognosis of AML patients is generally poor, especially for the elderly patients and those with poor physical condition.

FMS-like tyrosine kinase 3 (FLT3) is a type III receptor tyrosine kinase, which plays a key role in the proliferation, differentiation and apoptosis of hematopoietic cells and lymphocytes. The abnormal activation of FLT3 is closely related to the occurrence and development of AML. Studies have shown that more than one-third of the AML patients are accompanied by abnormal activation of FLT3.

The structure of FLT3 includes an extracellular domain, a transmembrane domain, and an intracellular tyrosine kinase domain that are composed of 5 immunoglobulin-like structures. FLT3 is mainly expressed on the cell surface of normal hematopoietic hepatocytes and hematopoietic progenitor cells, and its ligands are mainly expressed in the bone marrow stromal cells. When the ligand is bound to the extracellular domain of FLT3, the dimerization of FLT3 receptors and the autophosphorylation of the intracellular tyrosine kinase domain are promoted at the same time, activating a series of downstream signaling pathways, such as Ras/MAPK, PI3K/Akt/mTOR and STAT5, thereby regulating cell proliferation and differentiation. FLT3 mutations usually lead to its abnormal activation, and the autophosphorylation in the absence of binding with ligand, which activate the downstream signaling pathways, leading to the abnormal proliferation of hematopoietic cells and lymphocytes and triggering various malignant blood diseases.

There are two main types of FLT3 activation mutations, including the internal tandem duplication (ITD) mutations in the near-membrane domain and the point mutations of the activation loop in the tyrosine kinase domain (TKD).

The ITD mutation refers to an insertion of repeated tandem amino acid sequence in the near-membrane domain of FLT3. About 17% to 34% of AML patients are accompanied by this mutation, which is also detected in the myelodysplastic syndrome (MDS). Normally, the near-membrane domain has a self-inhibitory function on FLT3, which can inhibit the phosphorylation of the kinase domain. However, the ITD mutation may destroy the self-inhibitory activity of the near-membrane domain, resulting in the loss of the self-inhibition, and FLT3 is therefore in a continuously activated conformation. AML patients with the ITD mutation are often accompanied by the clinical features such as an increase in the number of leukocytes and an increase in the percentage of primitive bone marrow cells and blood cells. Due to the high rate of AML recurrence and many adverse reactions after the ITD mutation, the adverse prognosis of patients with ITD mutation is worse than that of ordinary AML patients.

The point mutations of FLT3 mainly occur in the activation loop of TKD. Insertion or deletion of exon 20 of FLT3 gene can make the 835 aspartic acid residue mutate at the C-terminal of TKD in FLT3, and about 7% of AML patients have this mutation. The most common mutation is Asp835Tyr, and other mutations such as Asp835Val, Asp835Glu and Asp835Asn are also found. These point mutations can stabilize the activation in the conformation of ATP binding, thereby enabling the continuous activation of FLT3.

Given that FLT3 plays a key role in the pathogenesis of AML, FLT3-targeted therapy has become the focus of anti-AML drug research.

AXL is a receptor-type tyrosine kinase, and is a protein having a cell transmembrane domain in the center, a tyrosine kinase domain on the carboxy-terminal side, and an extracellular domain on the amino-terminal side. So far, the overexpression of AXL has been reported in acute leukemia, astrocytoma, breast cancer, colorectal cancer, esophageal cancer, gastrointestinal stromal tumor, gastric cancer, hepatocellular carcinoma, Kaposi's sarcoma, lung cancer, melanoma, ovarian cancer, osteosarcoma, pancreatic ductal adenocarcinoma, renal cell carcinoma, prostate cancer, thyroid cancer, and endometrial cancer.

In addition, various cancers have been reported, in which AXL and resistance to chemotherapy are related. In the AML clinical samples, cells that have acquired resistance to chemotherapy also show the overexpression of AXL, and AML cell lines with stable expression of AXL also show the chemotherapy resistance. Therefore, AXL is considered to be the cause of drug resistance.

Gilteritinib (its chemical name is 6-ethyl-3-((3-methoxy-4-(4-(4-methylpiperazin-1-yl)piperidin-1-yl)phenyl) amino)-5-((tetrahydro-2H-pyra n-4-yl)amino)pyrazine-2-carboxamide with the following structural formula) is a FLT3 inhibitor developed by Astellas Pharma Inc. of Japan, which can effectively inhibit ITD and TKD, and is used in the treatment of adult patients with relapsed or refractory AML who are positive for FLT3 mutations. It can also inhibit kinases such as AXL. Clinical trials have shown that Gilteritinib can effectively inhibit the mutation and activity of FLT3, and can significantly prolong the life of patients at the same time. In July 2017, FDA granted it the orphan drug designation; in October 2017, FDA granted it the fast-track certification; and in November 2018, FDA approved it for marketing.

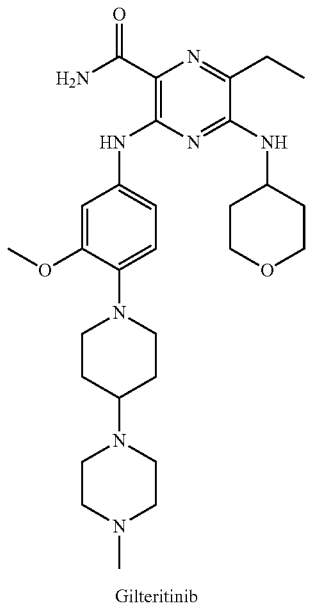 [SMILES: CCc1nc(C(N)=O)c(Nc2ccc(N3CCC(N4CCN(C)CC4)CC3)c(OC)c2)nc1NC1CCOCC1]

Gilteritinib

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism of many drugs, which could have been effective in treating diseases, could make them difficult to be used as drugs due to their rapid removal from the body. Although a frequent or high-dose administration may solve the problem of rapid drug clearance, this approach will bring problems such as poor compliance of patients, side effects caused by high-dose administration and increased treatment costs. In addition, drugs that are rapidly metabolized may also expose the patients to undesirable toxic or reactive metabolites.

Although Gilteritinib can treat AML effectively, there are serious unmet clinical needs in the treatment of AML patients with positive FLT3 mutations, and discovering novel compounds that can treat AML with good oral bioavailability and drugability is still a challenging task. Therefore, it is still necessary to develop compounds with selective inhibitory activity or better pharmacodynamic/pharmacokinetic properties as therapeutic agents for the FLT3 kinase-mediated diseases in this field. The present disclosure provides such compounds.

SUMMARY OF THE INVENTION

In view of the above technical problems, the present disclosure provides a new deuterated amino heterocyclic carboxamide compound, a composition comprising the same and use thereof. The compounds have better inhibitory activity against FLT3 and AXL kinases, lower side effects, higher selectivity, and better pharmacodynamic/pharmacokinetic properties, and can be used in treating cancers related to AML and others.

As used herein, the term "compound of the present disclosure" (or "compound disclosed herein") refers to the compounds represented by formula (Φ), (I) and (II). The term also includes pharmaceutically acceptable salts, prodrugs, hydrates, solvates, polymorphs, stereoisomers or isotopic variants of the compounds of formulae (Φ), (I) and (II).

In this regard, the technical solution adopted by the present disclosure is as follows:

In the first aspect, the present disclosure provides a compound of formula (Φ):

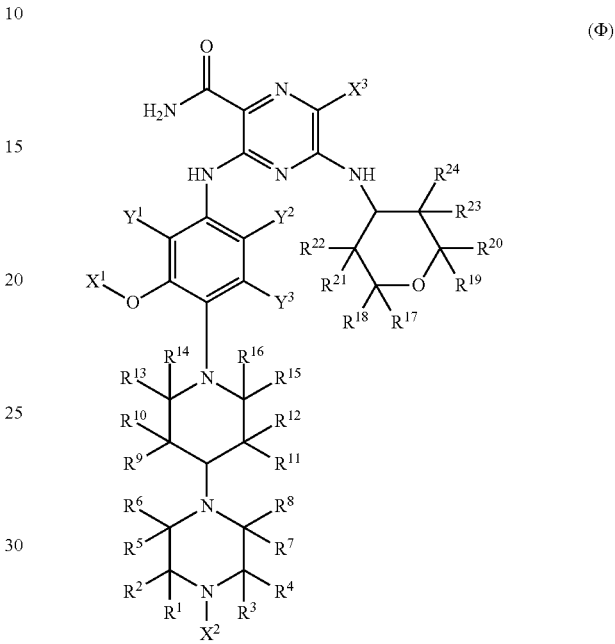

(Φ)

wherein,
$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ and $R^{24}$ are independently selected from hydrogen or deuterium;
$X^1$ and $X^2$ are independently selected from $CH_3$, $CD_3$, $CHD_2$ or $CH_2D$;
$X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$;
$Y^1$, $Y^2$ and $Y^3$ are independently selected from hydrogen or deuterium;
with the proviso that the compound described above contains at least one deuterium atom;
or a pharmaceutically acceptable salt, prodrug, hydrate, solvate, polymorph, stereoisomer or isotopic variant thereof.

In another aspect, the present disclosure provides a pharmaceutical composition, which comprises the compound of the present disclosure and pharmaceutically acceptable excipient(s). In a specific embodiment, the compound of the present disclosure is provided in an effective amount in the pharmaceutical composition. In a specific embodiment, the compound of the present disclosure is provided in a therapeutically effective amount. In a specific embodiment, the compound of the present disclosure is provided in a prophylactically effective amount.

In another aspect, the present disclosure provides a method of preparing the pharmaceutical composition described above, comprising the steps of: mixing the pharmaceutically acceptable excipient(s) with the compound of the present disclosure, thereby forming the pharmaceutical composition.

In another aspect, the present disclosure also provides a method of treating the FLT3 kinase-mediated disease in a subject. The method comprises administering to the subject a therapeutically effective amount of the compound disclosed herein. In a specific embodiment, the disease such as cancer is mediated by FLT3. In a specific embodiment, the patient is diagnosed or identified as having an FLT3-related cancer. In a specific embodiment, the FLT3-mediated disease is AML. In a specific embodiment, the compound is administered orally, subcutaneously, intravenously or intramuscularly. In a specific embodiment, the compound is administered chronically.

In another aspect, the present disclosure also provides a use of the compound disclosed herein in the preparation of a medicament for the treatment of diseases mediated by FLT3 kinase. The use includes administering to the subject a therapeutically effective amount of the compound disclosed herein. In a specific embodiment, the disease is mediated by FLT3. In a specific embodiment, the patient is diagnosed or identified as having an FLT3-related cancer. In a specific embodiment, the FLT3-mediated disease is AML. In a specific embodiment, the compound is administered orally, subcutaneously, intravenously or intramuscularly. In a specific embodiment, the compound is administered chronically.

In another aspect, the present disclosure also provides a method of treating the AXL kinase-related disease in a subject. The method includes administering to the subject a therapeutically effective amount of the compound disclosed herein. In a specific embodiment, the disease is mediated by AXL. In a specific embodiment, the patient is diagnosed or identified as having an AXL-related cancer. In a specific embodiment, the disease is a cancer with high expression of AXL. In a specific embodiment, the disease is a cancer that has acquired resistance to the anti-cancer drug treatment due to AXL activation. In a specific embodiment, the compound is administered orally, subcutaneously, intravenously or intramuscularly. In a specific embodiment, the compound is administered chronically.

In another aspect, the present disclosure also provides a use of the compound disclosed herein in the preparation of a medicament for the treatment of AXL kinase-related diseases. The method includes administering to the subject a therapeutically effective amount of the compound disclosed herein. In a specific embodiment, the disease is mediated by AXL. In a specific embodiment, the patient is diagnosed or identified as having an AXL-related cancer. In a specific embodiment, the disease is a cancer with high expression of AXL. In a specific embodiment, the disease is a cancer that has acquired resistance to the anti-cancer drug treatment due to AXL activation. In a specific embodiment, the compound is administered orally, subcutaneously, intravenously or intramuscularly. In a specific embodiment, the compound is administered chronically. Other objects and advantages of the present disclosure will be apparent to those skilled in the art from the subsequent specific embodiments, examples and claims.

DEFINITIONS

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound wherein the content of the deuterium atom is not higher than the natural content of the deuterium isotope (0.015%).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of the present disclosure include those derived from suitable inorganic and organic acids and inorganic and organic bases.

Also disclosed herein are isotopically labeled compounds to the extent of the original compounds disclosed herein. Examples of isotopes that can be listed in compounds disclosed herein include hydrogen, carbon, nitrogen, oxygen, phosphorus, sulfur, fluorine and chlorine isotopes, such as $^{2}H$, $^{13}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. A compound disclosed herein containing the above isotope or other isotopic atoms, or an enantiomer, a diastereomer, an isomer, or a pharmaceutically acceptable salt or a solvate thereof are all within the scope disclosed herein. Certain isotopically labeled compounds disclosed herein, such as the radioisotopes of $^{3}H$ and $^{14}C$, are also among them and are useful in the tissue distribution experiments of drugs and substrates. Tritium, i.e., $^{3}H$, and carbon-14, i.e., $^{14}C$, are easier to be prepared and detected and are the first choice for isotopes. Isotopically-labeled compounds can be prepared using the schemes shown in the Examples by conventional methods by replacing the non-isotopic reagents with readily available isotopically labeled reagents.

The compound disclosed herein may include one or more asymmetric centers, and thus may exist in a variety of "stereoisomer" forms, for example, enantiomeric and/or diastereomeric forms. For example, the compound disclosed herein may be in the form of an individual enantiomer, a diastereomer or a geometric isomer (e.g., cis- and trans-isomers), or may be in the form of a mixture of stereoisomers, including a racemic mixture and a mixture enriched in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

The compound disclosed herein may be in an amorphous or a crystalline form. In addition, the compound disclosed herein may exist in one or more crystalline forms. Therefore, the present disclosure includes all amorphous or crystalline forms of the compound disclosed herein within its scope. The term "polymorph" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

The term "solvate" refers to a complex in which a compound disclosed herein coordinates with a solvent molecule in a particular ratio. "Hydrate" refers to a complex formed by coordination of a compound disclosed herein with water.

The term "prodrug" as used herein refers to a compound, which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded compound disclosed herein which, when administered to a patient, releases the parent compound in vivo. A prodrug is typically prepared by modifying a functional group in such a way that the modification can be cleaved either by routine manipulation or decompose in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, the acetate/acetamide, formate/formamide and benzoate/benzamide derivatives of the hydroxyl, mercapto and amino functional groups of the compound of formula (I). Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those, which readily decompose in a human body to release a parent acid or its salt.

The term "polymorph" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

As used herein, the term "subject" includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats and/or dogs. In certain embodiments, the subject is a human. In certain embodiments, the subject is a non-human animal.

"Disease", "disorder" and "condition" are used interchangeably herein.

As used herein, and unless otherwise specified, the terms "treat," "treating," and "treatment" contemplate an action that occurs while a subject is suffering from a particular disease, disorder, or condition, which reduces the severity of the disease, disorder or condition, or retards or slows the progression of the disease, disorder or condition ("therapeutic treatment"). The term also contemplates an action that occurs before a subject begins to suffer from a specific disease, disorder or condition ("prophylactic treatment").

Generally, the "effective amount" of a compound refers to an amount sufficient to elicit a desired biological response. As will be appreciated by those skilled in the art, the effective amount of the compound disclosed herein can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

As used herein, and unless otherwise specified, the "therapeutically effective amount" of the compound is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

As used herein, and unless otherwise specified, the "prophylactically effective amount" of the compound is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the therapeutic agents disclosed herein. For example, the compounds of the present disclosure can be administered simultaneously or sequentially in separate unit dosage with other therapeutic agents, or simultaneously in a single unit dosage with other therapeutic agents.

DETAILED DESCRIPTION OF THE INVENTION

Compounds

The present disclosure provides a compound of formula (Φ), or a pharmaceutically acceptable salt, prodrug, hydrate, solvate, polymorph, stereoisomer or isotopic variant thereof:

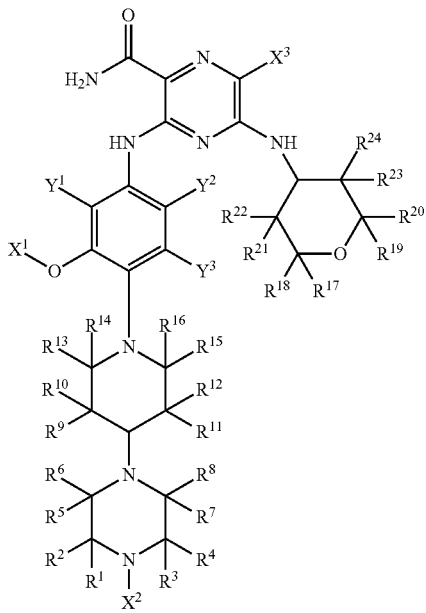

(Φ)

wherein, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}$ and $R^{24}$ are independently selected from hydrogen or deuterium;

$X^1$ and $X^2$ are independently selected from $CH_3$, $CD_3$, $CHD_2$ or $CH_2D$;

$X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$;

$Y^1$, $Y^2$ and $Y^3$ are independently selected from hydrogen or deuterium;

with the proviso that the compound described above contains at least one deuterium atom.

As a specific embodiment of the present disclosure, the compound of formula (D) contains at least one deuterium atom, alternatively two deuterium atoms, alternatively three deuterium atoms, alternatively four deuterium atoms, alternatively five deuterium atoms, alternatively six deuterium atoms, alternatively seven deuterium atoms, alternatively eight deuterium atoms, alternatively nine deuterium atoms, alternatively ten deuterium atoms, alternatively eleven deuterium atoms, alternatively twelve deuterium atoms, alternatively thirteen deuterium atoms, alternatively fourteen deuterium atoms, alternatively fifteen deuterium atoms, alternatively sixteen deuterium atoms, alternatively seventeen deuterium atoms, alternatively eighteen deuterium atoms, alternatively nineteen deuterium atoms, alternatively twenty deuterium atoms, alternatively twenty-one deuterium atoms, alternatively twenty-two deuterium atoms, alternatively twenty-three deuterium atoms, alternatively twenty-four deuterium atoms, alternatively twenty-five deuterium atoms, alternatively twenty-six deuterium atoms, alternatively twenty-seven deuterium atoms, alternatively twenty-eight deuterium atoms, alternatively twenty-nine deuterium atoms, alternatively thirty deuterium atoms, alternatively thirty-one deuterium atoms, alternatively thirty-two deuterium atoms, alternatively thirty-three deuterium atoms, alternatively thirty-four deuterium atoms, alternatively thirty-five deuterium atoms, alternatively thirty-six deuterium atoms, alternatively thirty-seven deuterium atoms, and alternatively thirty-eight deuterium atoms.

As an alternative embodiment of the present disclosure, the content of deuterium isotope in each deuterated position is at least greater than the natural content of deuterium isotope 0.015%, alternatively greater than 30%, alternatively greater than 50%, alternatively greater than 75%, alternatively greater than 95%, and alternatively greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $Y^1$, $Y^2$, $Y^3$, $X^1$, $X^2$ and $X^3$ is at least 5%, alternatively greater than 10%, alternatively greater than 15%, alternatively greater than 20%, alternatively greater than 25%, alternatively greater than 30%, alternatively greater than 35%, alternatively greater than 40%, alternatively greater than 45%, alternatively greater than 50%, alternatively greater than 55%, alternatively greater than 60%, alternatively greater than 65%, alternatively greater than 70%, alternatively greater than 75%, alternatively greater than 80%, alternatively greater than 85%, alternatively greater than 90%, alternatively greater than 95%, and alternatively greater than 99%.

In another specific embodiment, among $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $Y^1$, $Y^2$, $Y^3$, $X^1$, $X^2$ and $X^3$ of the compound of formula (Φ), at least one of them contains deuterium, alternatively two contain deuterium, alternatively three contain deuterium, alternatively four contain deuterium, alternatively five contain deuterium, alternatively six contain deuterium, alternatively seven contain deuterium, alternatively eight contain deuterium, alternatively nine contain deuterium, alternatively ten contain deuterium, alternatively eleven contain deuterium, alternatively twelve contain deuterium, alternatively thirteen contain deuterium, alternatively fourteen contain deuterium, alternatively fifteen contain deuterium, alternatively sixteen contain deuterium, alternatively seventeen contain deuterium, alternatively eighteen contain deuterium, alternatively nineteen contain deuterium, alternatively twenty contain deuterium, alternatively twenty-one contain deuterium, alternatively twenty-two contain deuterium, alternatively twenty-three contain deuterium, alternatively twenty-four contain deuterium, alternatively twenty-five contain deuterium, alternatively twenty-six contain deuterium, alternatively twenty-seven contain deuterium, alternatively twenty-eight contain deuterium, alternatively twenty-nine contain deuterium, alternatively thirty contain deuterium, alternatively thirty-one contain deuterium, alternatively thirty-two contain deuterium, alternatively thirty-three contain deuterium, alternatively thirty-four contain deuterium, alternatively thirty-five contain deuterium, alternatively thirty-six contain deuterium, alternatively thirty-seven contain deuterium, and alternatively thirty-eight contain deuterium. Specifically, the compound of formula (D) contains at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven and thirty-eight deuterium atoms.

In another specific embodiment, "$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ are independently selected from hydrogen or deuterium" includes the technical solutions wherein, $R^1$ is selected from hydrogen or deuterium, $R^2$ is selected from hydrogen or deuterium, R³ is selected from hydrogen or deuterium and so on, until R²⁴ is selected from hydrogen or deuterium. More specifically, the technical solutions wherein, R¹ is hydrogen or R¹ is deuterium, R² is hydrogen or R² is deuterium, R³ is hydrogen or R³ is deuterium and so on, until R²⁴ is hydrogen or R²⁴ is deuterium, are included.

In another specific embodiment, "X¹ and X² are independently selected from $CH_3$, $CD_3$, $CHD_2$ or $CH_2D$" includes the technical solutions wherein, X¹ is selected from $CH_3$, $CD_3$, $CHD_2$ or $CH_2D$, and X² is selected from $CH_3$, $CD_3$, $CHD_2$ or $CH_2D$. More specifically, the technical solutions wherein, X¹ is $CH_3$, X¹ is $CD_3$, X¹ is $CHD_2$ or X¹ is $CH_2D$, and X² is $CH_3$, X² is $CD_3$, X² is $CHD_2$ or X² is $CH_2D$, are included.

In another specific embodiment, "X³ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$" includes the technical solutions wherein, X³ is $CH_2CH_3$, X³ is $CH_2CH_2D$, X³ is $CH_2CHD_2$, X³ is $CH_2CD_3$, X³ is $CHDCH_3$, X³ is $CHDCH_2D$, X³ is $CHDCHD_2$, X³ is $CHDCD_3$, X³ is $CD_2CH_3$, X³ is $CD_2CH_2D$, X³ is $CD_2CHD_2$ or X³ is $CD_2CD_3$.

In another specific embodiment, "Y¹, Y² and Y³ are independently selected from hydrogen or deuterium" includes the technical solutions wherein, Y¹ is selected from hydrogen or deuterium, Y² is selected from hydrogen or deuterium, and Y³ is selected from hydrogen or deuterium. More specifically, the technical solutions wherein, Y¹ is hydrogen or Y¹ is deuterium, Y² is hydrogen or Y² is deuterium, and Y³ is hydrogen or Y³ is deuterium, are included.

In another embodiment, the present disclosure relates to a compound of formula (I):

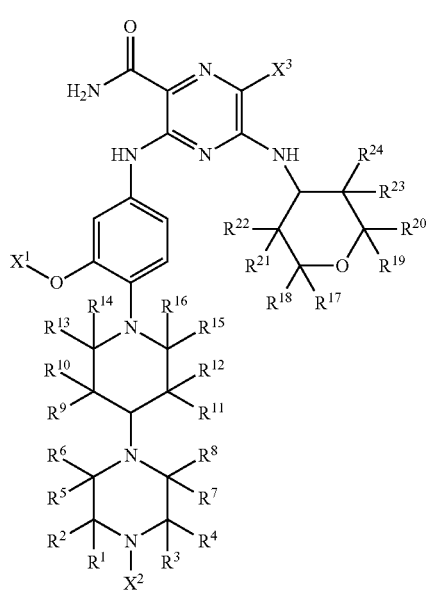

(I)

wherein,
R¹, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³ and R²⁴ are independently selected from hydrogen or deuterium;
X¹ and X² are independently selected from $CH_3$, $CD_3$, $CHD_2$ or $CH_2D$;

X³ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$;
with the proviso that the compound described above contains at least one deuterium atom;
or a pharmaceutically acceptable salt, prodrug, hydrate, solvate, polymorph, stereoisomer or isotopic variant thereof.

As a specific embodiment of the present disclosure, the compound of formula (I) contains at least one deuterium atom, alternatively one deuterium atom, alternatively two deuterium atoms, alternatively three deuterium atoms, alternatively four deuterium atoms, alternatively five deuterium atoms, alternatively six deuterium atoms, alternatively seven deuterium atoms, alternatively eight deuterium atoms, alternatively nine deuterium atoms, alternatively ten deuterium atoms, alternatively eleven deuterium atoms, alternatively twelve deuterium atoms, alternatively thirteen deuterium atoms, alternatively fourteen deuterium atoms, alternatively fifteen deuterium atoms, alternatively sixteen deuterium atoms, alternatively seventeen deuterium atoms, alternatively eighteen deuterium atoms, alternatively nineteen deuterium atoms, alternatively twenty deuterium atoms, alternatively twenty-one deuterium atoms, alternatively twenty-two deuterium atoms, alternatively twenty-three deuterium atoms, alternatively twenty-four deuterium atoms, alternatively twenty-five deuterium atoms, alternatively twenty-six deuterium atoms, alternatively twenty-seven deuterium atoms, alternatively twenty-eight deuterium atoms, alternatively twenty-nine deuterium atoms, alternatively thirty deuterium atoms, alternatively thirty-one deuterium atoms, alternatively thirty-two deuterium atoms, alternatively thirty-three deuterium atoms, alternatively thirty-four deuterium atoms, and alternatively thirty-five deuterium atoms.

As an alternative embodiment of the present disclosure, the content of deuterium isotope in each deuterated position is at least greater than the natural content of deuterium isotope 0.015%, alternatively greater than 30%, alternatively greater than 50%, alternatively greater than 75%, alternatively greater than 95%, and alternatively greater than 99%.

Specifically, in the present disclosure, the content of the deuterium isotope in each deuterated position of R, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³, R²⁴, X¹, X² and X³ is at least 5%, alternatively greater than 10%, alternatively greater than 15%, alternatively greater than 20%, alternatively greater than 25%, alternatively greater than 30%, alternatively greater than 35%, alternatively greater than 40%, alternatively greater than 45%, alternatively greater than 50%, alternatively greater than 55%, alternatively greater than 60%, alternatively greater than 65%, alternatively greater than 70%, alternatively greater than 75%, alternatively greater than 80%, alternatively greater than 85%, alternatively greater than 90%, alternatively greater than 95%, and alternatively greater than 99%.

In another specific embodiment, among R¹, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³, R²⁴, X¹, X² and X³ of the compound of formula (I), at least one of them contains deuterium, alternatively two contain deuterium, alternatively three contain deuterium, alternatively four contain deuterium, alternatively five contain deuterium, alternatively six contain deuterium, alternatively seven contain deuterium, alternatively eight contain deuterium, alternatively nine contain deuterium, alternatively ten contain deuterium, alternatively eleven contain deuterium, alternatively twelve contain deuterium, alternatively thirteen contain deuterium, alternatively fourteen contain deuterium, alternatively fifteen contain deuterium, alternatively sixteen contain deuterium, alternatively seventeen contain deuterium, alternatively eighteen contain deuterium, alternatively nineteen contain deuterium, and alternatively twenty contain deuterium. Specifically, the compound of formula (I) contains at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven and thirty-eight deuterium atoms.

As a specific embodiment of the present disclosure, $X^1$ and $X^2$ are independently selected from $CH_3$, $CD_3$, $CHD_2$ or $CH_2D$. In another specific embodiment, $X^1$ and $X^2$ are independently selected from $CH_3$ or $CD_3$. In another specific embodiment, $X^1$ is $CH_3$. In another specific embodiment, $X^1$ is $CD_3$. In another specific embodiment, $X^2$ is $CH_3$. In another specific embodiment, $X^2$ is $CD_3$. In another specific embodiment, $X^1$ and $X^2$ are the same. In another embodiment, $X^1$ and $X^2$ are different.

As a specific embodiment of the present disclosure, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$. In another specific embodiment, $X^3$ is selected from $CH_2CH_3$ or $CD_2CD_3$. In another specific embodiment, $X^3$ is $CH_2CH_3$. In another specific embodiment, $X^3$ is $CD_2CD_3$.

As a specific embodiment of the present disclosure, $R^1$, $R^2$, $R^3$, $R^4$, $R^5$, $R^6$, $R^7$ and $R^8$ are independently selected from hydrogen or deuterium. In another specific embodiment, $R^1$, $R^2$, $R^3$, $R^4$, $R^5$, $R^6$, $R^7$ and $R^8$ are the same. In another specific embodiment, $R^1$, $R^2$, $R^3$, $R^4$, $R^5$, $R^6$, $R^7$ and $R^8$ are hydrogen. In another specific embodiment, $R^1$, $R^2$, $R^3$, $R^4$, $R^5$, $R^6$, $R^7$ and $R^8$ are deuterium.

As a specific embodiment of the present disclosure, $R^9$, $R^{10}$, $R^{11}$, $R^{12}$, $R^{13}$, $R^{14}$, $R^{15}$ and $R^{16}$ are independently selected from hydrogen or deuterium. In another specific embodiment, $R^9$, $R^{10}$, $R^{11}$ and $R^{12}$ are the same, and $R^{13}$, $R^{14}$, $R^{15}$ and $R^{16}$ are the same. In another specific embodiment, $R^9$, $R^{10}$, $R^{11}$, $R^{12}$, $R^{13}$, $R^{14}$, $R^{15}$ and $R^{16}$ are hydrogen. In another specific embodiment, $R^9$, $R^{10}$, $R^{11}$, $R^{12}$, $R^{13}$, $R^{14}$, $R^{15}$ and $R^{16}$ are deuterium. In another specific embodiment, $R^9$, $R^{10}$, $R^{11}$ and $R^{12}$ are deuterium, and $R^{13}$, $R^{14}$, $R^{15}$ and $R^{16}$ are hydrogen. In another specific embodiment, $R^9$, $R^{10}$, $R^{11}$ and $R^{12}$ are hydrogen, and $R^{13}$, $R^{14}$, $R^{15}$ and $R^{16}$ are deuterium.

In a specific embodiment, the present disclosure relates to a compound of formula (I), or a pharmaceutically acceptable salt, prodrug, hydrate, solvate, polymorph, stereoisomer or isotopic variant thereof, wherein, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (I), or a pharmaceutically acceptable salt, prodrug, hydrate, solvate, polymorph, stereoisomer or isotopic variant thereof, wherein, $R^1$ to $R^8$ are hydrogen, $R^9$ to $R^{24}$ are independently selected from hydrogen or deuterium, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (I), or a pharmaceutically acceptable salt, prodrug, hydrate, solvate, polymorph, stereoisomer or isotopic variant thereof, wherein, $R^1$ to $R^{12}$ are hydrogen, $R^{13}$ to $R^{24}$ are independently selected from hydrogen or deuterium, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $R^1$ to $R^{24}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $R^1$ to $R^8$ are hydrogen, $R^9$ to $R^{24}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $R^1$ to $R^{12}$ are hydrogen, $R^{13}$ to $R^{24}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $R^1$ to $R^{24}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $R^1$ to $R^8$ are hydrogen, $R^9$ to $R^{24}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $R^1$ to $R^{12}$ are hydrogen, $R^{13}$ to $R^{24}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $R^1$ to $R^{24}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $R^1$ to $R^8$ are hydrogen, $R^9$ to $R^{24}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $R^1$ to $R^{12}$ are hydrogen, $R^{13}$ to $R^{24}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (I), or a pharmaceutically acceptable salt, prodrug, hydrate, solvate, polymorph, stereoisomer or isotopic variant thereof, wherein, $X^3$ is $CD_2CD_3$, $R^1$ to $R^{24}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^3$ is $CD_2CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^3$ is $CD_2CD_3$, $R^1$ to $R^8$ are hydrogen, $R^9$ to $R^{24}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^3$ is $CD_2CD_3$, $R^1$ to $R^{12}$ are hydrogen, $R^{13}$ to $R^{24}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^3$ is $CD_2CD_3$, $X^2$ is $CD_3$, $R^1$ to $R^{24}$ are independently selected from hydrogen or deuterium, $X^1$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^1$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^1$ to $R^8$ are hydrogen, $R^9$ to $R^{24}$ are independently selected from hydrogen or deuterium, $X^1$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^1$ to $R^{12}$ are hydrogen, $R^{13}$ to $R^{24}$ are independently selected from hydrogen or deuterium, $X^1$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^{24}$ are independently selected from hydrogen or deuterium, $X^2$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium, $X^2$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^8$ are hydrogen, $R^9$ to $R^{24}$ are independently selected from hydrogen or deuterium, $X^2$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^{12}$ are hydrogen, $R^{13}$ to $R^{24}$ are independently selected from hydrogen or deuterium, $X^2$ is selected from $CH_3$, $CD_3$, $CHD_2$ or $CH_2D$.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^{24}$ are independently selected from hydrogen or deuterium.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^9$ to $R^{12}$ are hydrogen, $R^1$ to $R^8$ are independently selected from hydrogen or deuterium, $R^{13}$ to $R^{24}$ are independently selected from hydrogen or deuterium.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^8$ are hydrogen, $R^9$ to $R^{24}$ are independently selected from hydrogen or deuterium.

In another specific embodiment, the present disclosure relates to a compound of formula (I), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^{12}$ are hydrogen, $R^{13}$ to $R^{24}$ are independently selected from hydrogen or deuterium.

In another embodiment, the present disclosure relates to a compound of formula (II):

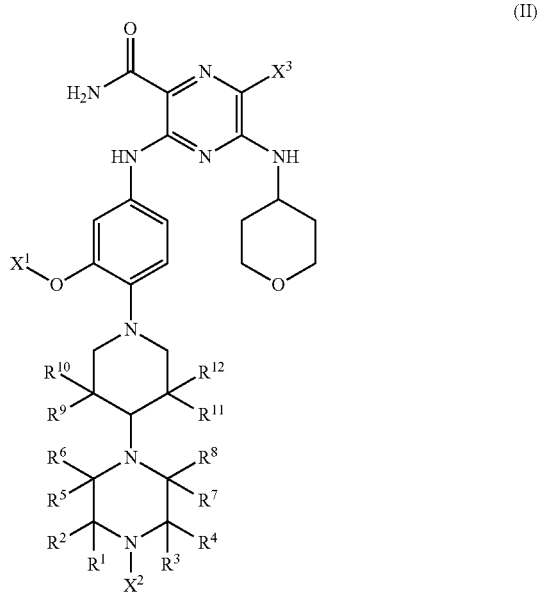

(II)

wherein,
$R^1$, $R^2$, $R^3$, $R^4$, $R^5$, $R^6$, $R^7$, $R^8$, $R^9$, $R^{10}$, $R^{11}$ and $R^{12}$ are independently selected from hydrogen or deuterium;
$X^1$ and $X^2$ are independently selected from $CH_3$, $CD_3$, $CHD_2$ or $CH_2D$;
$X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$;
with the proviso that the compound described above contains at least one deuterium atom;
or a pharmaceutically acceptable salt, prodrug, hydrate, solvate, polymorph, stereoisomer or isotopic variant thereof.

In a specific embodiment, the present disclosure relates to a compound of formula (II), or a pharmaceutically acceptable salt, prodrug, hydrate, solvate, polymorph, stereoisomer or isotopic variant thereof, wherein, $R^9$ to $R^{12}$ are hydrogen, $R^1$ to $R^8$ are independently selected from hydrogen or deuterium, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (II), or a pharmaceutically acceptable salt, prodrug, hydrate, solvate, polymorph, stereoisomer or isotopic variant thereof, wherein, $R^1$ to $R^8$ are hydrogen, $R^9$ to $R^{12}$ are independently selected from hydrogen or deuterium, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (II), or a pharmaceutically acceptable salt, prodrug, hydrate, solvate, polymorph, stereoisomer or isotopic variant thereof, wherein, $R^1$ to $R^{12}$ are hydrogen, $X^1$ and $X^2$ are independently selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$, with the proviso that the compound described above contains at least one deuterium atom.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $R^1$ to $R^{12}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $R^9$ to $R^{12}$ are hydrogen, $R^1$ to $R^8$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $R^1$ to $R^8$ are hydrogen, $R^9$ to $R^{12}$ are independently selected from hydrogen or deuterium, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $R^1$ to $R^{12}$ are hydrogen, $X^1$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $R^1$ to $R^{12}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $R^9$ to $R^{12}$ are hydrogen, $R^1$ to $R^8$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $R^1$ to $R^8$ are hydrogen, $R^9$ to $R^{12}$ are independently selected from hydrogen or deuterium, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $R^1$ to $R^{12}$ are hydrogen, $X^2$ is selected from $CH_3$, $CD_3$, $CHD_2$ or $CH_2D$, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $R^1$ to $R^{12}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $R^9$ to $R^{12}$ are hydrogen, $R^1$ to $R^8$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $R^1$ to $R^8$ are hydrogen, $R^9$ to $R^{12}$ are independently selected from hydrogen or deuterium, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $R^1$ to $R^{12}$ are hydrogen, $X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$.

In another specific embodiment, the present disclosure relates to a compound of formula (II), or a pharmaceutically acceptable salt, prodrug, hydrate, solvate, polymorph, stereoisomer or isotopic variant thereof, wherein, $X^3$ is $CD_2CD_3$, $R^1$ to $R^{12}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^3$ is $CD_2CD_3$, $R^9$ to $R^{12}$ are hydrogen, $R^1$ to $R^8$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^3$ is $CD_2CD_3$, $R^1$ to $R^8$ are hydrogen, $R^9$ to $R^{12}$ are independently selected from hydrogen or deuterium, $X^1$ and $X^2$ are independently selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^3$ is $CD_2CD_3$, $R^1$ to $R^{12}$ are hydrogen, $X^1$ and $X^2$ are independently selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^3$ is $CD_2CD_3$, $X^2$ is $CD_3$, $R^1$ to $R^{12}$ are independently selected from hydrogen or deuterium, $X^1$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^9$ to $R^{12}$ are hydrogen, $R^1$ to $R^8$ are independently selected from hydrogen or deuterium, $X^1$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^1$ to $R^8$ are hydrogen, $R^9$ to $R^{12}$ are independently selected from hydrogen or deuterium, $X^1$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^2$ is $CD_3$, $X^3$ is $CD_2CD_3$, $R^1$ to $R^{12}$ are hydrogen, $X^1$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^{12}$ are independently selected from hydrogen or deuterium, $X^2$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^9$ to $R^{12}$ are hydrogen, $R^1$ to $R^8$ are independently selected from hydrogen or deuterium, $X^2$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^8$ are hydrogen, $R^9$ to $R^{12}$ are independently selected from hydrogen or deuterium, $X^2$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ is $CD_3$, $X^3$ is $CD_2CD_3$, $R^1$ to $R^{12}$ are hydrogen, $X^2$ is selected from $CH_3$, $CD_3$, $CHD_2$ or $CH_2D$.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^{12}$ are independently selected from hydrogen or deuterium.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^9$ to $R^{12}$ are hydrogen, $R^1$ to $R^8$ are independently selected from hydrogen or deuterium.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^8$ are hydrogen, $R^9$ to $R^{12}$ are independently selected from hydrogen or deuterium.

In another specific embodiment, the present disclosure relates to a compound of formula (II), or a pharmaceutically acceptable salt, prodrug, hydrate, solvate, polymorph, stereoisomer or isotopic variant thereof, wherein, $X^1$ and $X^2$ are $CD_3$, $X^3$ is $CD_2CD_3$, $R^1$ to $R^{12}$ are hydrogen.

As an alternative embodiment of the present disclosure, the compound is selected from the following group of compounds:

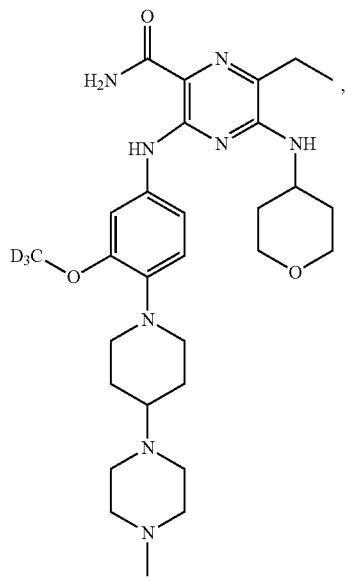

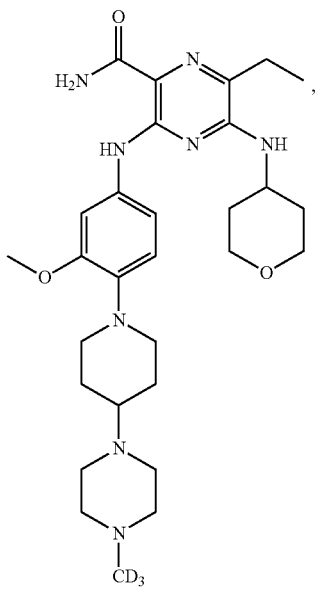

23
-continued
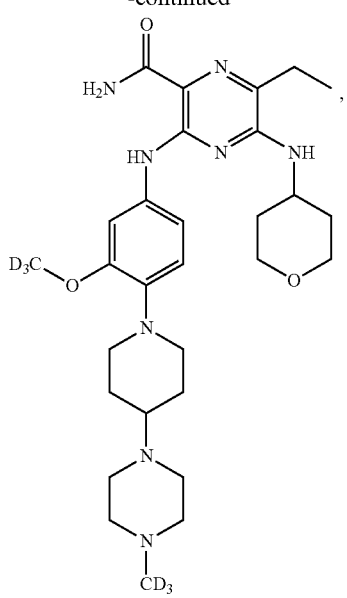
24
-continued
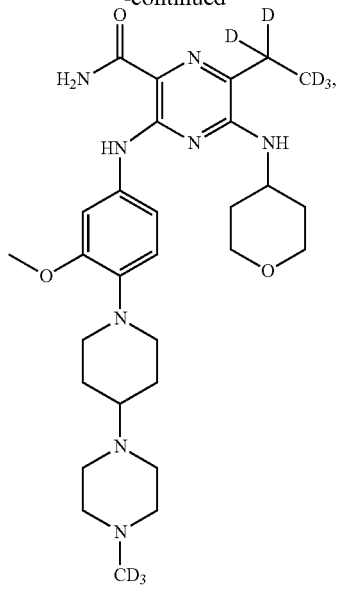
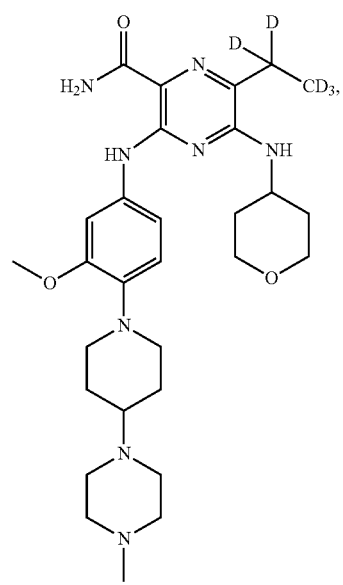

25
-continued
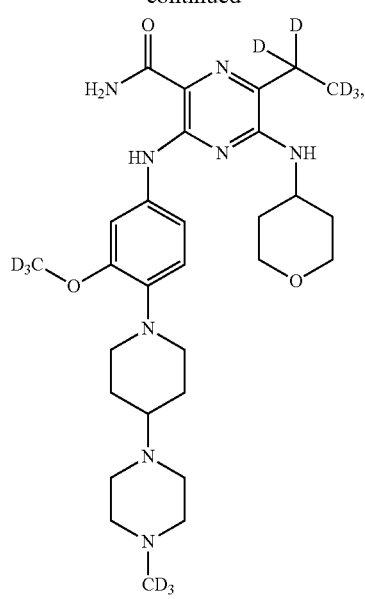
26
-continued
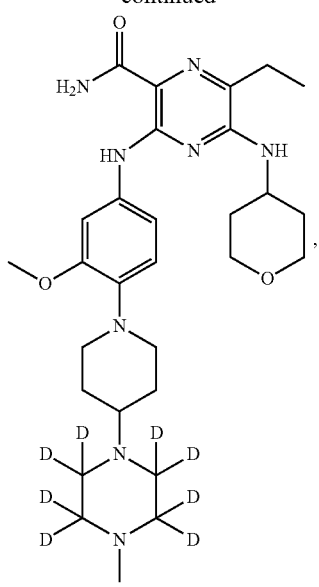
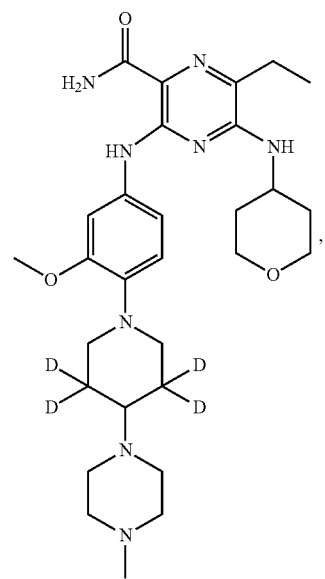
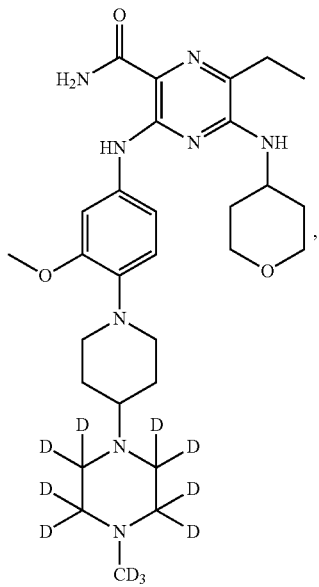

27
-continued
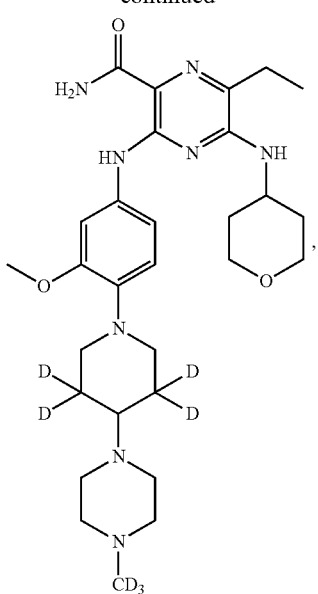
28
-continued
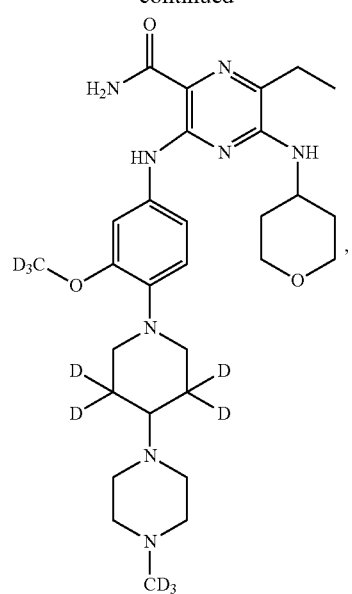
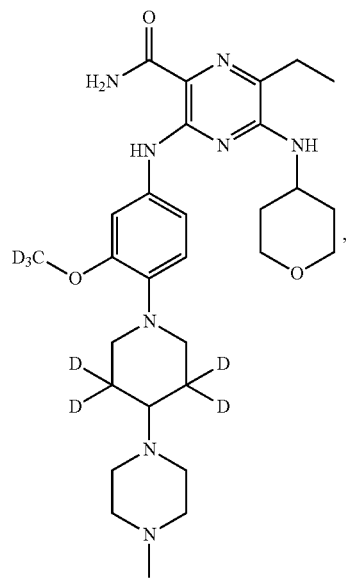
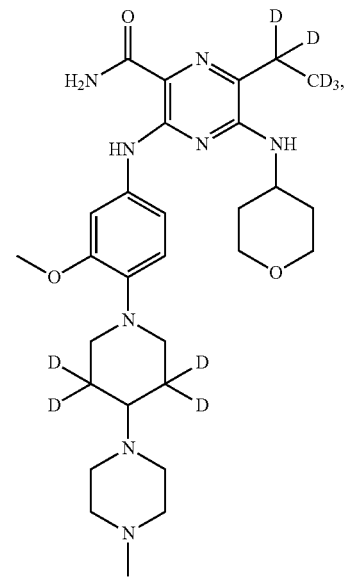

29
-continued
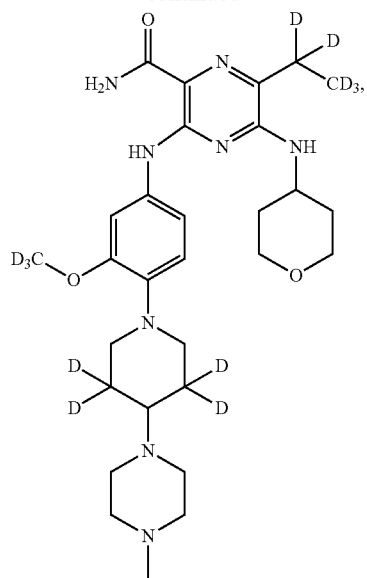
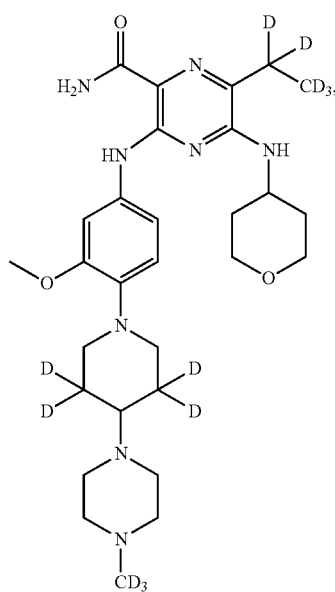
30
-continued
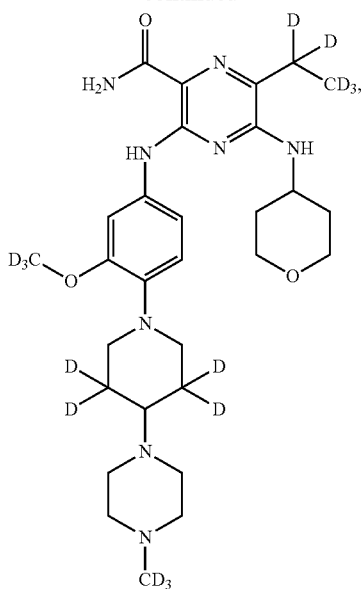
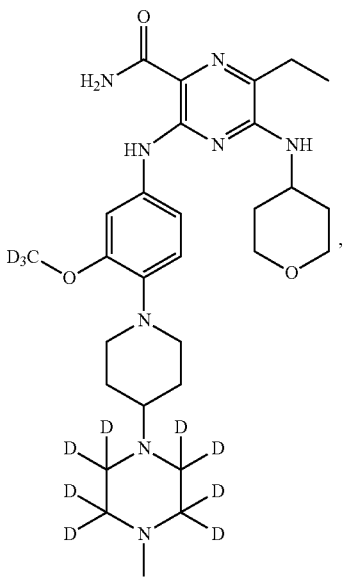

31
-continued
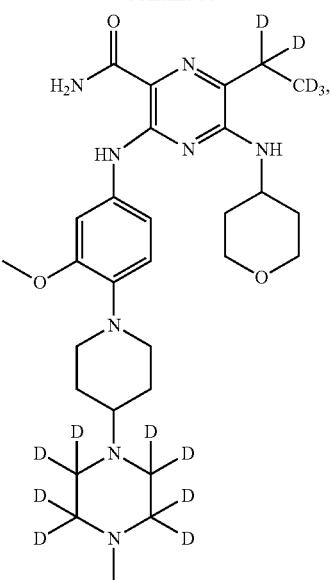
32
-continued
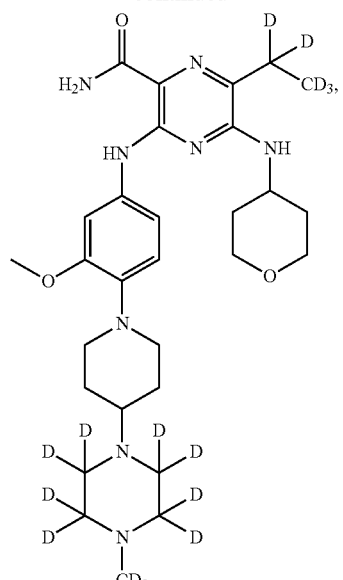
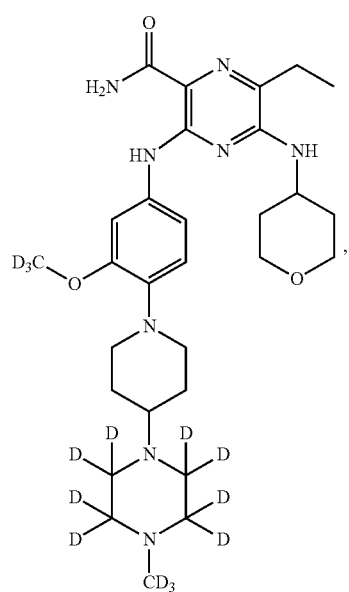

-continued

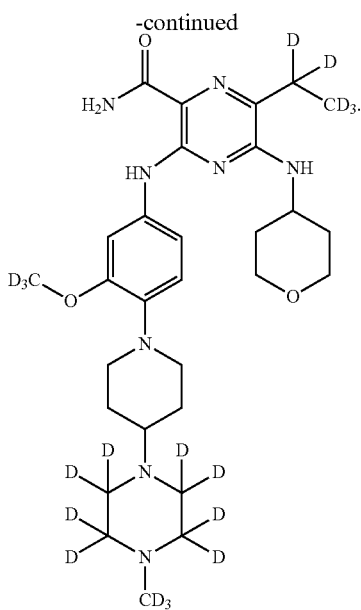

As an alternative embodiment of the present disclosure, the compounds do not include the non-deuterated compounds.

Pharmaceutical Compositions and Methods of Administration

In another aspect, provided herein is a pharmaceutical composition comprising the compound disclosed herein (also referred to as "active component") and pharmaceutically acceptable excipient(s). In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The pharmaceutical composition disclosed herein comprises a safe and effective amount of the compound disclosed herein, or a pharmacologically acceptable salt thereof, and pharmacologically acceptable excipient(s) or carrier(s). By "safe and effective amount" it is meant that the amount of the compound is sufficient to significantly improve the condition without causing serious side effects. In general, the pharmaceutical composition contains from 0.5 to 2000 mg of the compound disclosed herein per dose, more preferably from 1 to 500 mg of the compound disclosed herein per dose. Preferably, the "one dose" is one capsule or tablet.

The "pharmaceutically acceptable excipient" refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The pharmaceutical composition disclosed herein can be prepared by combining the compound disclosed herein with suitable pharmaceutically acceptable excipient(s), for example, as a solid, semi-solid, liquid or gaseous preparation such as tablets, pills, capsules, powders, granules, ointments, emulsions, suspensions, solutions, suppositories, injections, inhalants, gels, microspheres, aerosols and the like.

Typical routes of administration of the compound disclosed herein or a pharmaceutical composition thereof include, but are not limited to, oral, rectal, transmucosal, enteral administration, or topical, transdermal, inhalation, parenteral, sublingual, intravaginal, intranasal, intraocular, intraperitoneal, intramuscular, subcutaneous, intravenous administration.

The pharmaceutical composition disclosed herein can be produced by a method well known in the art, such as a conventional mixing method, a dissolution method, a granulation method, a sugarcoating pill method, a grinding method, an emulsification method, a freeze drying method, and the like.

For oral administration, the pharmaceutical composition can be formulated by mixing the active compound with pharmaceutically acceptable excipient(s) which are well known in the art. These excipients enable the compound disclosed herein to be formulated into tablets, pills, troches, dragees, capsules, liquids, gels, slurries, suspensions and the like for oral administration to a patient.

A solid oral composition can be prepared by a conventional mixing, filling or tabletting method. For example, it can be obtained by mixing the active compound with solid excipient(s), optionally milling the resulting mixture, adding other suitable adjuvant(s) if necessary, and then processing the mixture into granules, thereby obtaining a tablet or a core of dragee. Suitable excipients include, but are not limited to, binders, diluents, disintegrants, lubricants, glidants, sweeteners or flavoring agents, and the like, such as microcrystalline cellulose, glucose solution, acacia mucilage, gelatin solution, sucrose and starch paste; talc, starch, calcium stearate or stearic acid; lactose, sucrose, starch, mannitol, sorbitol or dicalcium phosphate; silica; cross-linked hydroxymethylcellulose sodium, pregelatinized starch, sodium starch glycolate, alginic acid, corn starch, potato starch, methyl cellulose, agar, hydroxymethyl cellulose, cross-linked polyvinyl pyrrolidone and the like. The core of the dragee may optionally be coated according to methods well known in the ordinary pharmaceutical practice, especially using enteric coatings.

The pharmaceutical compositions may also be suitable for parenteral administration, such as sterile solutions, suspensions or lyophilized products in a suitable unit dosage form. Suitable excipients such as fillers, buffers or surfactants can be used.

The compounds disclosed herein may be administered by any route and method of administration, for example by oral or parenteral (e.g., intravenous) administration. A therapeutically effective amount of the compound disclosed herein is from about 0.0001 to 20 mg/kg body weight per day, such as from 0.001 to 10 mg/kg body weight per day.

The dosing frequency of the compounds disclosed herein is determined by the needs of the individual patient, for example, once or twice daily, or more times per day. Administration may be intermittent, for example, wherein the patient receives a daily dose of the compound disclosed herein for a period of several days, and then the patient does not receive a daily dose of the compound disclosed herein for a period of several days or more.

Therapeutic Indications of the Compound Disclosed Herein

The compound of the present disclosure shows the inhibitory effect against FLT3 protein tyrosine kinase, and can be used in the treatment of FLT3-mediated diseases.

In some embodiments, the present disclosure provides a method of treating the FLT3 kinase-mediated disease in a subject. The method comprises administering to the subject a therapeutically effective amount of the compound disclosed herein. In a specific embodiment, the disease is mediated by FLT3. In a specific embodiment, the patient is diagnosed or identified as having an FLT3-related cancer. In a specific embodiment, the compound is administered orally, subcutaneously, intravenously or intramuscularly. In a specific embodiment, the compound is administered chronically. In a specific embodiment, the FLT3-mediated disease is AML.

In some embodiments, the present disclosure provides a method of treating AXL-related cancer. The method comprises administering to the subject a therapeutically effective amount of the compound disclosed herein. AXL is a receptor-type tyrosine kinase, and is a protein having a cell transmembrane domain in the center, a tyrosine kinase domain on the carboxy-terminal side, and an extracellular domain on the amino-terminal side. AXL-related cancer refers to the cancer wherein one of the causes thereof is AXL. As cancers with highly expressed AXL, examples such as AML, astrocytoma, breast cancer, colorectal cancer, gastrointestinal stromal tumor, gastric cancer, hepatocellular carcinoma, Kaposi's sarcoma, lung cancer, melanoma, ovarian cancer, osteosarcoma, pancreatic ductal adenocarcinoma, renal cell carcinoma, prostate cancer, thyroid cancer, and endometrial cancer, in which AXL is overexpressed compared to normal tissues, can be listed.

Compared with the non-deuterated compounds known in the prior art, the compounds of the present disclosure have a series of advantages. The advantages of the present disclosure include: first, the compounds and compositions of the technical solutions disclosed herein provide a more advantageous therapeutic tool for the treatment of AML, especially for the treatment of FLT3- and AXL-related AML. Second, the metabolism of the compound in the organism is improved, allowing the compound to have better pharmacokinetic parameters. In this case, the dose may be changed and a long-acting formulation may be formed to improve the applicability. Third, the drug concentration of the compound in animals is increased, so that the efficacy of the drug is improved. Fourth, the safety of the compound may be increased due to the inhibition of certain metabolites.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

Usually, in the preparation process, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1 Preparation of 6-ethyl-3-((3-(methoxy-d$_3$)-4-(4-(4-methylpiperazin-1-yl)piperidin-1-yl)phenyl)amino)-5-((tetrahydro-2H-pyran-4-yl)amino)pyrazine-2-carboxamide (Compound T-1)

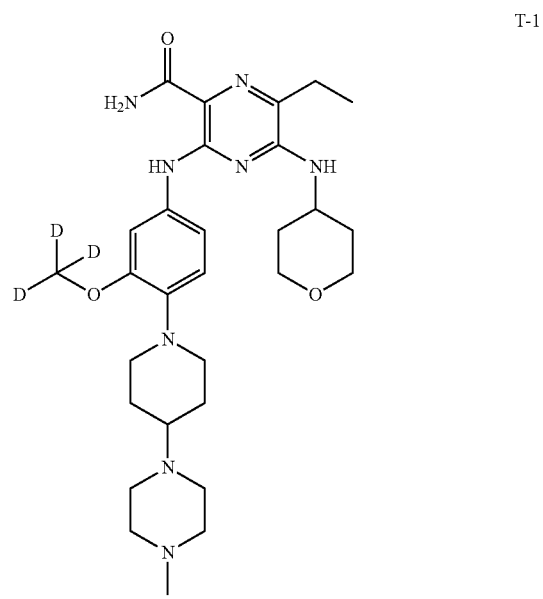 [SMILES: [2H]C([2H])([2H])Oc1cc(Nc2nc(NC3CCOCC3)c(CC)nc2C(N)=O)ccc1N1CCC(N2CCN(C)CC2)CC1]

T-1

The following route was used for the synthesis:

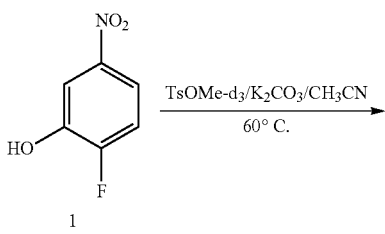

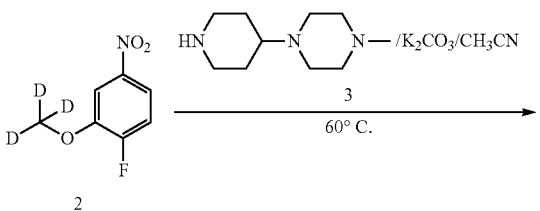

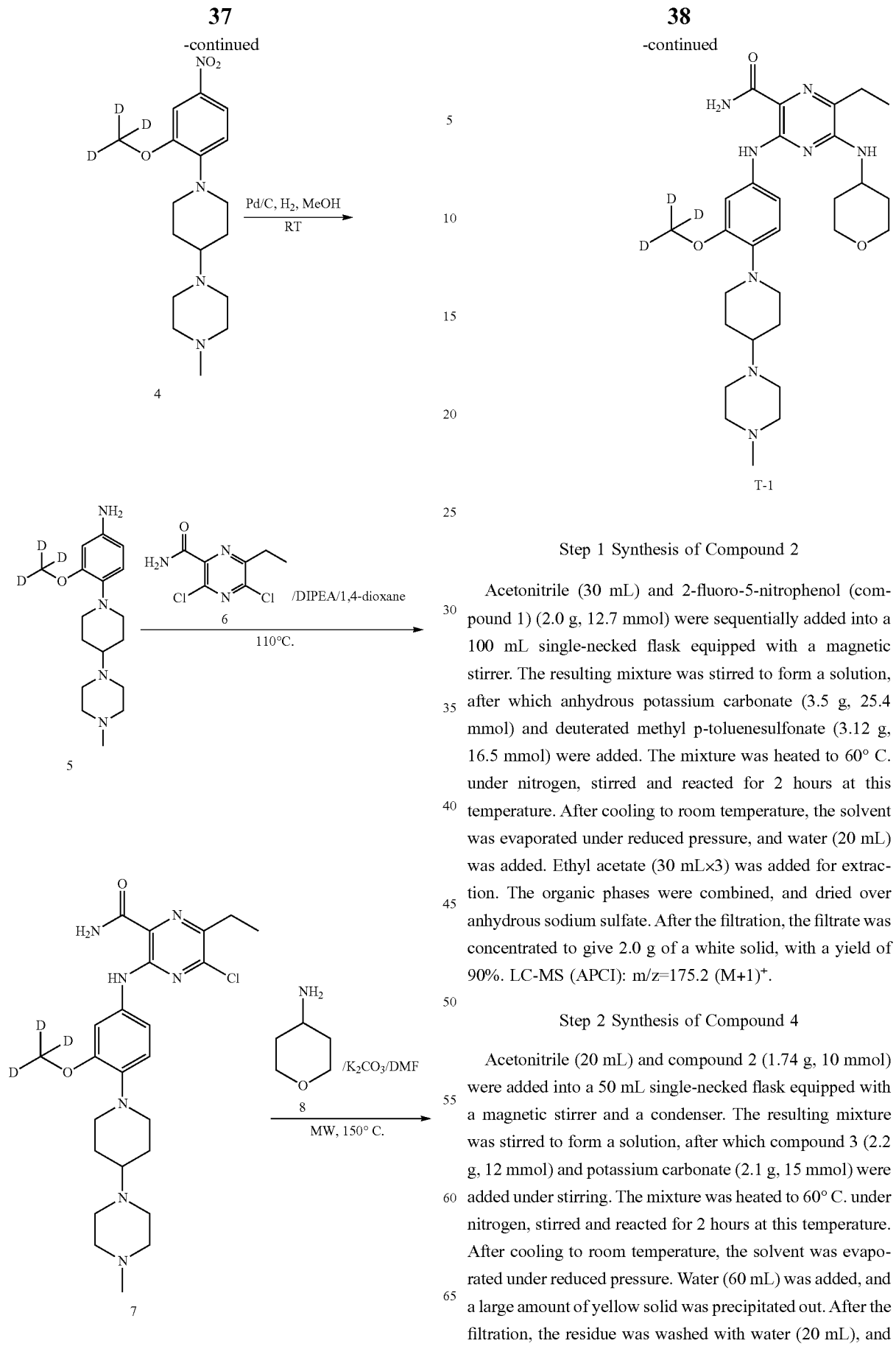

Step 1 Synthesis of Compound 2

Acetonitrile (30 mL) and 2-fluoro-5-nitrophenol (compound 1) (2.0 g, 12.7 mmol) were sequentially added into a 100 mL single-necked flask equipped with a magnetic stirrer. The resulting mixture was stirred to form a solution, after which anhydrous potassium carbonate (3.5 g, 25.4 mmol) and deuterated methyl p-toluenesulfonate (3.12 g, 16.5 mmol) were added. The mixture was heated to 60° C. under nitrogen, stirred and reacted for 2 hours at this temperature. After cooling to room temperature, the solvent was evaporated under reduced pressure, and water (20 mL) was added. Ethyl acetate (30 mL×3) was added for extraction. The organic phases were combined, and dried over anhydrous sodium sulfate. After the filtration, the filtrate was concentrated to give 2.0 g of a white solid, with a yield of 90%. LC-MS (APCI): m/z=175.2 (M+1)$^+$.

Step 2 Synthesis of Compound 4

Acetonitrile (20 mL) and compound 2 (1.74 g, 10 mmol) were added into a 50 mL single-necked flask equipped with a magnetic stirrer and a condenser. The resulting mixture was stirred to form a solution, after which compound 3 (2.2 g, 12 mmol) and potassium carbonate (2.1 g, 15 mmol) were added under stirring. The mixture was heated to 60° C. under nitrogen, stirred and reacted for 2 hours at this temperature. After cooling to room temperature, the solvent was evaporated under reduced pressure. Water (60 mL) was added, and a large amount of yellow solid was precipitated out. After the filtration, the residue was washed with water (20 mL), and dried to give 2.6 g of a yellow solid, with a yield of 77.1%. LC-MS (APCI): m/z=338.2 (M+1)+.

Step 3 Synthesis of Compound 5

Compound 4 (1.34 g, 4.0 mmol) and methanol (20 mL) were added into a 50 mL single-necked flask equipped with a magnetic stirrer, and stirred to form a solution. Pd/C (0.12 g, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 1.18 g of a light brown solid, with a yield of 98.2%. LC-MS (APCI): m/z=308.2 (M+1)+.

Step 4 Synthesis of Compound 7

Compound 5 (0.62 g, 2.0 mmol) and 1,4-dioxane (10 mL) were added into a 50 mL single-necked flask equipped with a magnetic stirrer and a condenser. The resulting mixture was stirred to form a solution, after which compound 6 (0.50 g, 2.28 mmol) and DIPEA (N,N-diisopropylethylamine, 0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.82 g of a yellow solid, with a yield of 83.7%. LC-MS (APCI): m/z=491.3 (M+1)+. $^1$H NMR (500 MHz, CDCl$_3$) δ (ppm): 10.75 (s, 1H), 7.72 (s, 1H), 7.35 (d, J=2.0 Hz, 1H), 7.13 (dd, J=9.5 Hz, J=2.0 Hz, 1H), 6.88 (d, J=9.5 Hz, 1H), 5.55 (s, 1H), 3.53 (d, J=11.5 Hz, 2H), 2.99-2.75 (m, 10H), 2.57 (t, J=11.5 Hz, 2H), 2.49 (s, 3H), 2.05-1.95 (m, 2H), 1.90-1.82 (m, 2H), 1.27 (t, J=7.0 Hz, 3H).

Step 5 Synthesis of Compound T-1

Compound 7 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=556.3 (M+1)+. $^1$H NMR (400 MHz, CDCl$_3$) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.57-3.51 (m, 4H), 3.15-2.75 (m, 8H), 2.62-2.49 (m, 7H), 2.10-1.98 (m, 4H), 1.88-1.85 (m, 2H), 1.62-1.60 (m, 2H), 1.34-1.29 (m, 3H).

Example 2 Preparation of 6-ethyl-3-((3-methoxy-4-(4-(4-(methyl-d$_3$)piperazin-1-yl)piperidin-1-yl)phenyl)amino)-5-((tetrahydro-2H-pyran-4-yl)amino)pyrazine-2-carboxamide (Compound T-2)

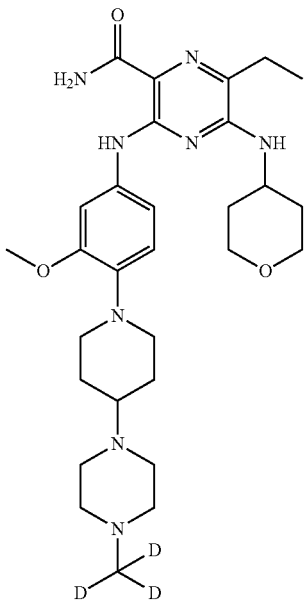

The following route was used for the synthesis:

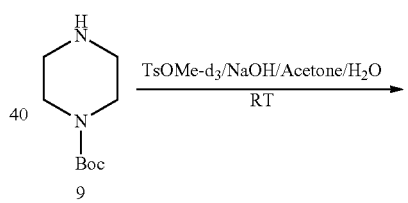

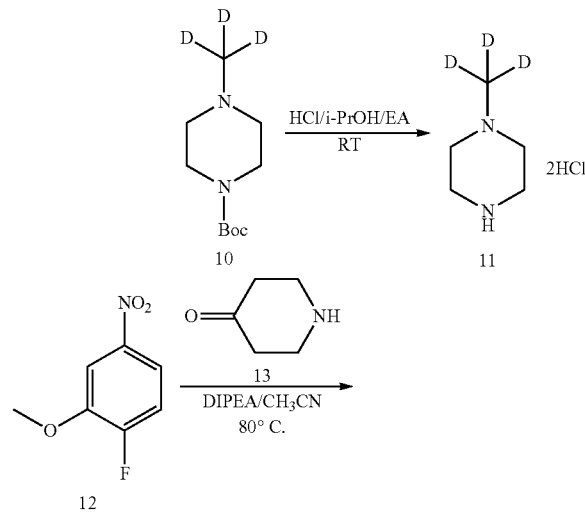

-continued

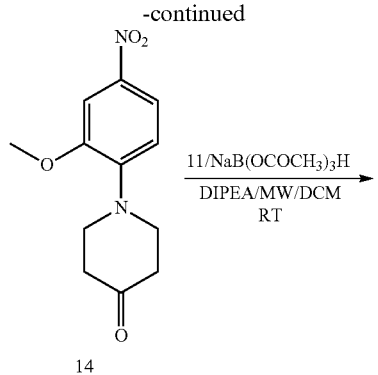

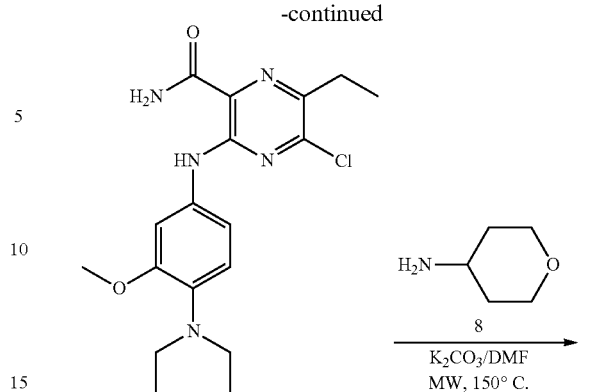

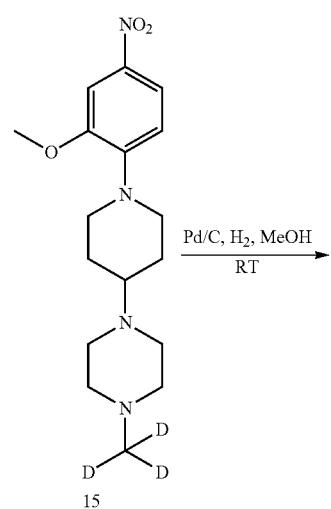

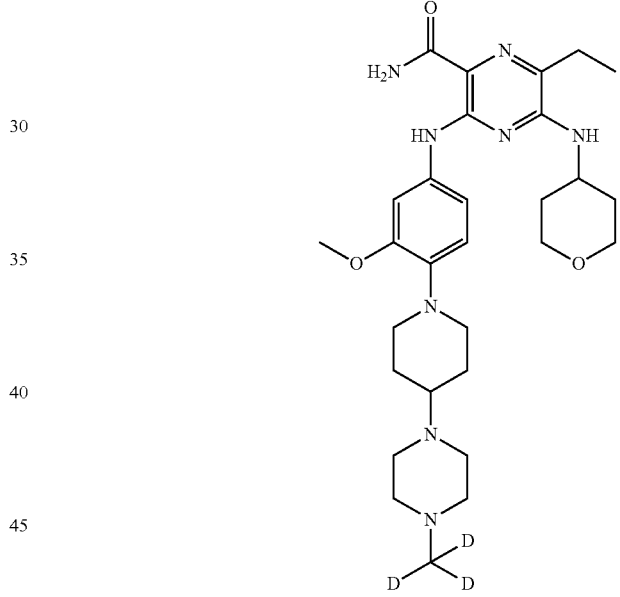

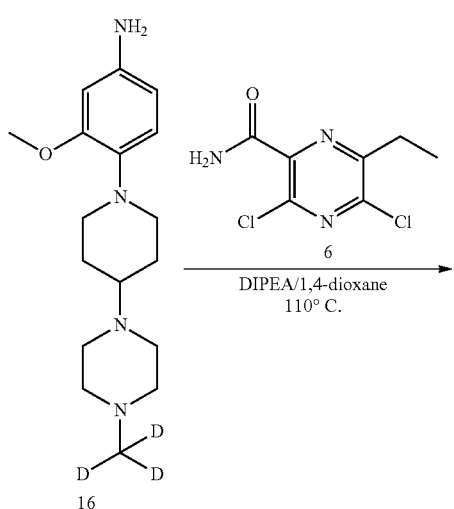

Step 1 Synthesis of Compound 10

Solid sodium hydroxide (11.2 g, 0.28 mol) was slowly added to water (100 mL) under stirring, which was stirred to form a solution. The resulting mixture was cooled to below 10° C. in an ice-water bath, and compound 9 (50 g, 0.27 mol) was added. A solution of methyl-$d_3$ p-toluenesulfonate (53.32 g, 0.28 mol) in acetone (250 mL) was slowly added dropwise, stirred and reacted overnight at room temperature. Di-tert-butyl dicarbonate (3.42 g, 0.013 mol) was added to the reaction solution, and further stirred and reacted for 1 h. Acetone was evaporated under reduced pressure at room temperature, and the residue was extracted with ethyl acetate (150 mL×3). The organic phases were combined, washed with water (50 mL×3), saturated sodium carbonate (50 mL), saturated brine (50 mL), and dried over anhydrous sodium sulfate. After the filtration, the filtrate was concentrated under reduced pressure to approximately 250 mL, and cooled in an ice-water bath. A solution of hydrogen chloride in isopropanol (5 M) was slowly added dropwise, during which the temperature was controlled below 10° C. The pH was adjusted to 4, and a large amount of white solid was generated. After stirring for half an hour under nitrogen, the resulting mixture was filtered. The filter cake was washed with ethyl acetate (50 mL), and dried in vacuum to give 38 g of a white solid, with a yield of 61.6%. $^1$H NMR (400 MHz, DMSO-d6) δ (ppm): 11.45 (br s, 1H), 3.97-3.95 (m, 2H), 3.33-3.29 (m, 4H), 2.95-2.93 (m, 2H), 1.41 (s, 9H).

Step 2 Synthesis of Compound 11

A solution of hydrogen chloride in isopropanol (210 mL, 5 M) was added to the compound 10 (50 g, 0.21 mol) under stirring in an ice-water bath, and the resulting mixture was stirred and reacted for 4 hours under nitrogen. Ethyl acetate (400 mL) was added, and stirred for half an hour. After the filtration, the filter cake was washed with ethyl acetate (50 mL), and was put into a flask under nitrogen. The ethyl acetate was evaporated under reduced pressure to give 30 g of product, with a yield of 82.2%.

Step 3 Synthesis of Compound 14

Compound 12 (5.0 g, 29.2 mmol) was added to acetonitrile (40 mL) in a 100 mL single-necked flask equipped with a magnetic stirrer and a condenser, and stirred to form a solution. 4-Piperidone hydrochloride monohydrate (compound 13) (5.38 g, 35.1 mmol) and DIPEA (11.3 g, 87.7 mol) were sequentially added, and the reaction mixture was heated to 80° C. under nitrogen, at which the mixture was stirred and reacted overnight. After cooling to room temperature, the acetonitrile was evaporated under reduced pressure. The residue was poured into cold water (200 mL) under stirring, and a large amount of yellow solid was precipitated out, after which the mixture was stirred for half an hour. After the filtration, the filter cake was washed with water (100 mL), and dried in vacuum. The resulting solid was added to n-hexane (50 mL), heated to reflux for 1 h under stirring, and cooled to room temperature. After the filtration, the residue was dried to give 6.20 g of a yellow solid, with a yield of 84.8%. LC-MS (APCI): m/z=251.2 (M+1)$^+$.

Step 4 Synthesis of Compound 15

Compound 14 (1.81 g, 7.2 mmol) and dichloromethane (18 mL) were added into a 100 mL single-necked flask equipped with a magnetic stirrer and a condenser, and stirred to form a solution. Compound 11 (1.66 g, 9.4 mmol) and DIPEA (2.43 g, 18.8 mol) were sequentially added, and stirred for 10 minutes to form a solution. Powder 4 Å molecular sieve (1.44 g) was added, and stirred for 10 minutes. Sodium triacetoxyborohydride (3.05 g, 14.4 mol) was added in one portion, stirred and reacted overnight under the protection of nitrogen. Water (40 mL) was added, and stirred for 20 minutes. Then the molecular sieve was filtered off through celite, after which the water phase was separated from the filtrate, and the dichloromethane phase was extracted with water (10 mL×3). The water phases were combined, and ammonia (28%-30%) was added dropwise to adjust the pH to 10. Dichloromethane (60 mL×3) was added for back extraction. The dichloromethane phases were combined, washed with saturated brine (20 mL), and dried over anhydrous sodium sulfate. After the filtration, the filtrate was concentrated to dryness to give 2.1 g of a yellow solid, with a yield of 86.5%. LC-MS (APCI): m/z=338.2 (M+1)$^+$.

Step 5 Synthesis of Compound 16

Compound 15 (1.34 g, 4.0 mmol) and methanol (20 mL) were added into a 50 mL single-necked flask equipped with a magnetic stirrer, and stirred to form a solution. Pd/C (0.12 g, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 1.18 g of a light brown solid, with a yield of 98.2%. LC-MS (APCI): m/z=308.2 (M+1)$^+$.

Step 6 Synthesis of Compound 17

Compound 16 (0.62 g, 2.0 mmol) and 1,4-dioxane (10 mL) were added into a 50 mL single-necked flask equipped with a magnetic stirrer and a condenser. The resulting mixture was stirred to form a solution, after which compound 6 (0.50 g, 2.28 mmol) and DIPEA (0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.82 g of a yellow solid, with a yield of 83.7%. LC-MS (APCI): m/z=491.3 (M+1)$^+$. $^1$H NMR (500 MHz, CDCl$_3$) δ (ppm): 10.69 (s, 1H), 7.72 (s, 1H), 7.35 (d, J=2.0 Hz, 1H), 7.13 (dd, J=9.5 Hz, J=2.0 Hz, 1H), 6.88 (d, J=9.5 Hz, 1H), 5.55 (s, 1H), 3.89 (s, 3H), 3.53 (d, J=11.5 Hz, 2H), 3.12-2.88 (m, 7H), 2.85 (q, J=7.0 Hz, 2H), 2.57 (t, J=11.5 Hz, 2H), 2.05-1.95 (m, 2H), 1.90-1.82 (m, 2H), 1.27 (t, J=7.0 Hz, 3H).

Step 7 Synthesis of Compound T-2

Compound 17 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=556.3 (M+1)$^+$. $^1$H NMR (300 MHz, CDCl$_3$) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.87 (s, 3H), 3.57-3.51 (m, 4H), 3.15-2.75 (m, 8H), 2.62-2.49 (m, 7H), 2.10-1.98 (m, 4H), 1.88-1.85 (m, 2H), 1.62-1.60 (m, 2H), 1.34-1.29 (m, 3H).

Example 3 Preparation of 6-ethyl-3-((3-(methoxy-d$_3$)-4-(4-(4-(methyl-d$_3$)piperazin-1-yl)piperidin-1-yl)phenyl)amino)-5-((tetrahydro-2H-pyran-4-yl)amino)pyrazine-2-carboxamide (Compound T-3)
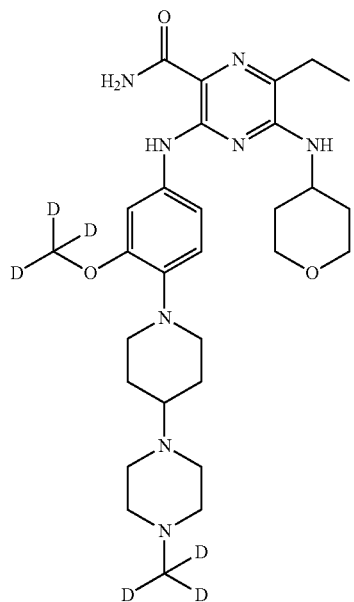
T-3
The following route was used for the synthesis:
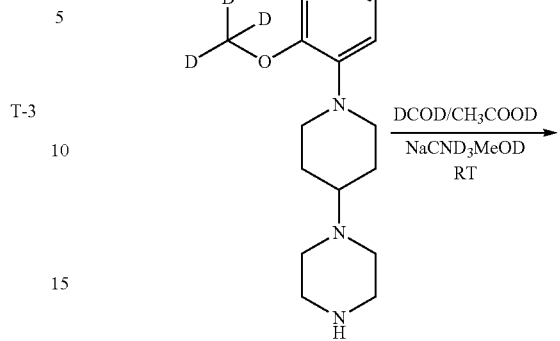
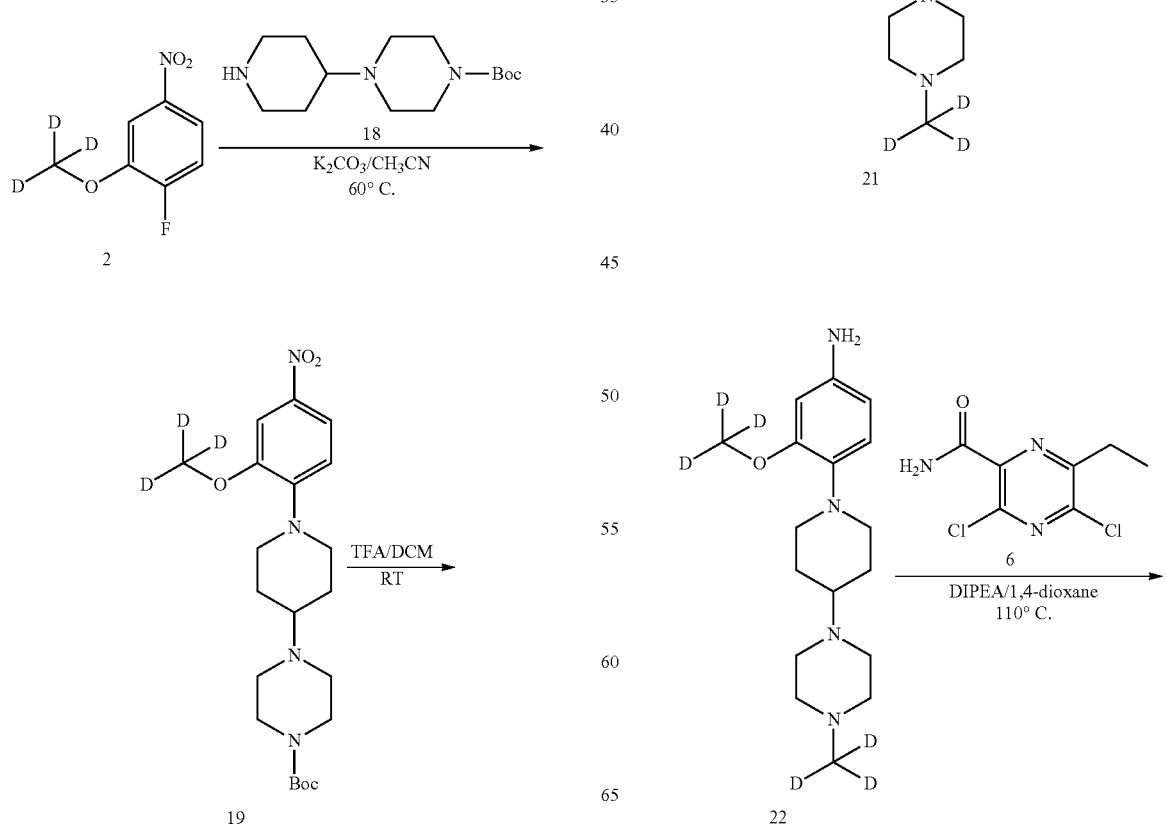

47

-continued

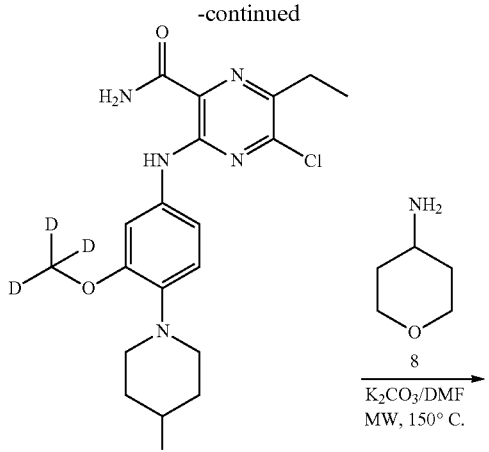

23

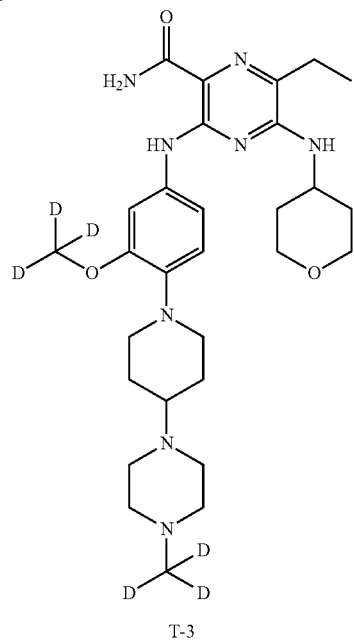

T-3

Step 1 Synthesis of Compound 19

Acetonitrile (20 mL) and compound 2 (1.74 g, 10 mmol) were added into a 50 mL single-necked flask equipped with a magnetic stirrer and a condenser. The resulting mixture was stirred to form a solution, after which compound 18 (3.2 g, 12 mmol) and potassium carbonate (2.1 g, 15 mmol) were added under stirring. The mixture was heated to 60° C. under nitrogen, stirred and reacted for 2 hours at this temperature. After cooling to room temperature, the solvent was evaporated under reduced pressure. Water (60 mL) was added, and a large amount of yellow solid was precipitated out. After the filtration, the residue was washed with water (20 mL), and dried to give 2.8 g of a yellow solid, with a yield of 66.2%. LC-MS (APCI): m/z=424.2 (M+1)$^+$.

48

Step 2 Synthesis of Compound 20

Compound 19 (2.8 g, 6.6 mmol) and dichloromethane (30 mL) were added into a 50 mL single-necked flask equipped with a magnetic stirrer, and stirred to form a solution. Trifluoroacetic acid (10 mL) was added dropwise under stirring, and the resulting mixture was stirred and reacted for 2 hours at room temperature under nitrogen. The solvent was evaporated to dryness under reduced pressure, and dichloromethane (30 mL) was added. A solution of ammonia in methanol (7 M) was added dropwise under stirring, and the pH was adjusted to 10. After stirring for 10 minutes, the generated ammonium chloride solid was filtered off, and the filtrate was concentrated under reduced pressure to give 2.0 g of a yellow solid, with a yield of 93.9%. LC-MS (APCI): m/z=324.2 (M+1)$^+$.

Step 3 Synthesis of Compound 21

Compound 20 (1.0 g, 3.13 mmol) and MeOD (10 mL) were added into a 50 mL single-necked flask equipped with a magnetic stirrer, and stirred to form a solution. A solution of deuterated formaldehyde in heavy water (0.56 g, 3.76 mmol, 20% w/w) and three drops of $CH_3COOD$ were added dropwise, which was stirred for 10 minutes under nitrogen. Deuterated sodium cyanoborohydride (0.31 g, 4.70 mmol) was added, and further stirred and reacted for 1 hour. Saturated aqueous solution of sodium bicarbonate (20 mL) was added to quench the reaction, and the resulting mixture was extracted with dichloromethane (30 mL×3). The organic phases were combined, washed with saturated brine (20 mL), and dried over anhydrous sodium sulfate. After the filtration and concentration, the residue was purified by silica gel column chromatography to give 0.85 g of a yellow solid, with a yield of 80.6%. LC-MS (APCI): m/z=341.2 (M+1)$^+$.

Step 4 Synthesis of Compound 22

Compound 21 (0.68 g, 2.0 mmol) and methanol (10 mL) were added into a 50 mL single-necked flask equipped with a magnetic stirrer, and stirred to form a solution. Pd/C (70 mg, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 0.6 g of a light brown solid, with a yield of 98.2%. LC-MS (APCI): m/z=311.2 (M+1)$^+$.

Step 5 Synthesis of Compound 23

Compound 22 (0.6 g, 2.0 mmol) and 1,4-dioxane (10 mL) were added into a 50 mL single-necked flask equipped with a magnetic stirrer and a condenser. The resulting mixture was stirred to form a solution, after which compound 6 (0.50 g, 2.28 mmol) and DIPEA (0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.82 g of a yellow solid, with a yield of 83.7%. LC-MS (APCI): m/z=494.3 (M+1)$^+$. $^1$H NMR (500 MHz, CDCl$_3$) δ (ppm): 10.75 (s, 1H), 7.72 (s, 1H), 7.35 (d, J=2.0 Hz, 1H), 7.13 (dd, J=9.5 Hz, J=2.0 Hz, 1H), 6.88 (d, J=9.5 Hz, 1H), 5.55 (s, 1H), 3.53 (d, J=11.5 Hz, 2H), 2.99-2.75 (m, 10H), 2.57 (t, J=11.5 Hz, 2H), 2.05-1.95 (m, 2H), 1.90-1.82 (m, 2H), 1.27 (t, J=7.0 Hz, 3H).

Step 6 Synthesis of Compound T-3

Compound 23 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=559.3 (M+1)+. 1H NMR (400 MHz, CDCl₃) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.57-3.51 (m, 4H), 3.15-2.75 (m, 8H), 2.62-2.49 (m, 5H), 2.10-1.98 (m, 4H), 1.88-1.85 (m, 2H), 1.62-1.60 (m, 2H), 1.34-1.29 (m, 3H).

Example 4 Preparation of 6-(ethyl-d₅)-3-((3-methoxy-4-(4-(4-methylpiperazin-1-yl)piperidin-1-yl)phenyl)amino)-5-((tetrahydro-2H-pyran-4-yl)amino)pyrazine-2-carboxamide (Compound T-4)

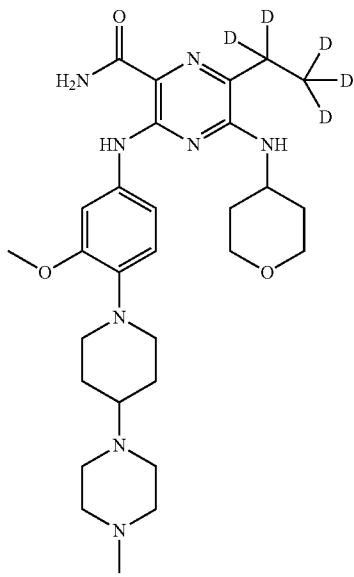

T-4

The following route was used for the synthesis:

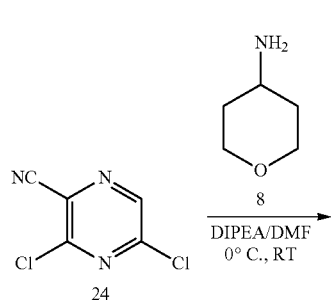

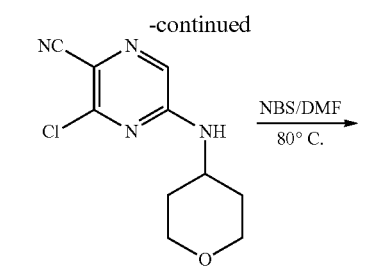

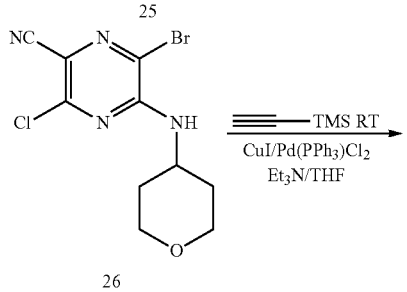

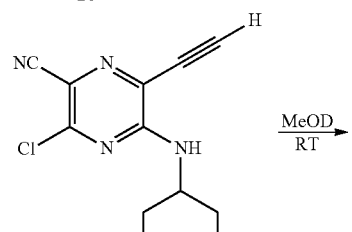

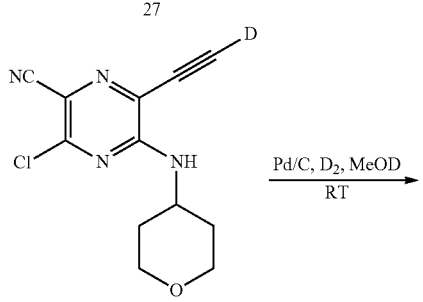

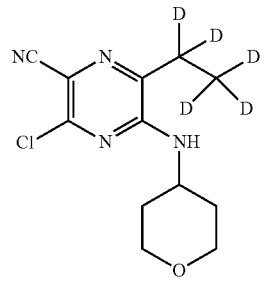

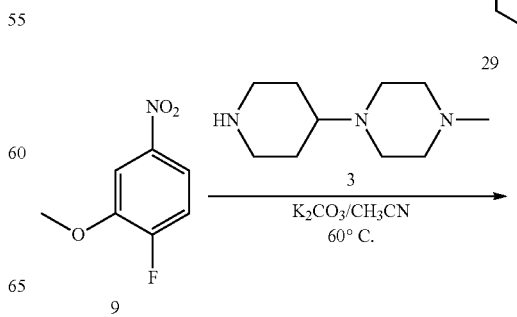

-continued

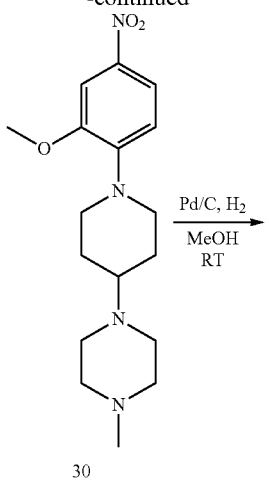

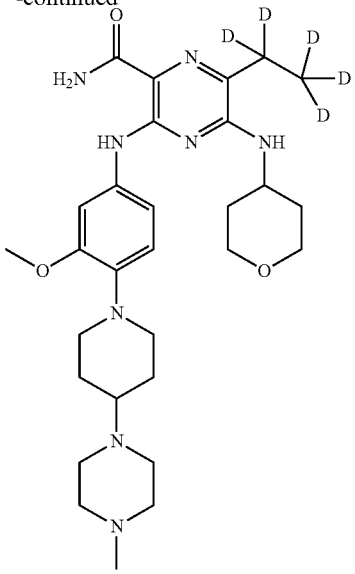

T-4

Step 1 Synthesis of Compound 25

Compound 24 (1.72 g, 10 mmol) and DMF (20 mL) were added into a 50 mL single-necked flask equipped with a magnetic stirrer, and stirred to form a solution. Compound 8 (1.0 g, 10 mmol) and DIPEA (1.93 g, 15 mmol) were added dropwise in an ice-water bath, after which, the ice-water bath was removed, and the mixture was stirred and reacted for 2 hours at room temperature under nitrogen. Water (100 mL) was added to quench the reaction. The resulting mixture was extracted with ethyl acetate (80 mL×2), washed with water (100 mL×3), washed with saturated brine (50 mL), and dried over anhydrous sodium sulfate. After the filtration and concentration, the residue was purified by silica gel column chromatography to give 1.8 g of a yellow solid, with a yield of 75.6%. LC-MS (APCI): m/z=239.2 (M+1)$^+$. $^1$H NMR (500 MHz, CDCl3) δ ppm: 7.78 (s, 1H), 5.27 (br s, 1H), 4.13-4.10 (m, 1H), 4.04-4.00 (m, 2H), 3.57-3.52 (m, 2H), 2.05-2.01 (m, 2H), 1.63-1.54 (m, 2H).

Step 2 Synthesis of Compound 26

Compound 25 (1.5 g, 6.3 mmol) and DMF (10 mL) were added into a 50 mL single-necked flask equipped with a magnetic stirrer, and stirred to form a solution. NBS (N-bromosuccinimide, 1.57 g, 8.8 mmol) was added. The resulting mixture was heated to 80° C. under nitrogen, stirred and reacted for 2 hours at this temperature. The solvent was evaporated under reduced pressure, and the residue was purified by silica gel column chromatography to give 1.7 g of a white solid, with a yield of 81.5%. LC-MS (APCI): m/z=317.1 (M+1)$^+$. $^1$H NMR (300 MHz, CDCl3) δ (ppm): 5.80 (d, J=6.6 Hz, 1H), 4.24-4.16 (m, 1H), 4.07-4.02 (m, 2H), 3.61-3.52 (m, 2H), 2.07-2.02 (m, 2H), 1.71-1.62 (m, 2H).

Step 3 Synthesis of Compound 27

Compound 26 (1.5 g, 4.74 mmol), CuI (8.9 mg, 0.095 mmol) and bis(triphenylphosphine)palladium dichloride (66

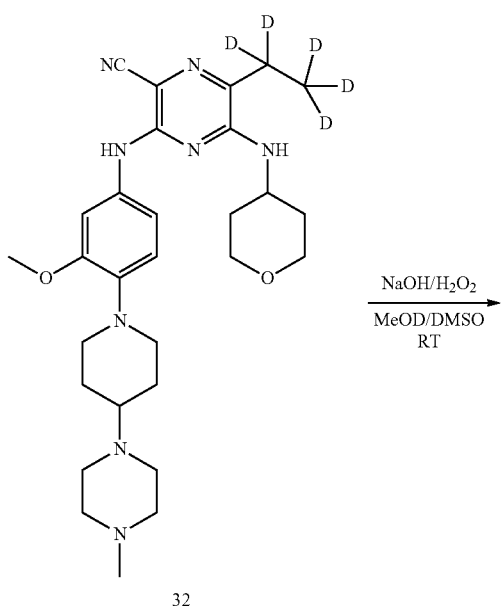

mg, 0.095 mmol) were added into a 100 mL double-necked flask equipped with a magnetic stirrer. The resulting mixture was vacuumed and purged with nitrogen for three times. Anhydrous THF (30 mL), triethylamine (0.96 g, 9.5 mmol) and trimethylsilylacetylene (0.55 g, 5.69 mmol) were sequentially added through syringe under nitrogen, after which, the mixture was stirred and reacted for 2 hours at room temperature under nitrogen. Dichloromethane (50 mL) was added, and the insoluble solid was filtered off. The solvent was evaporated under reduced pressure, and the residue was purified by silica gel column chromatography to give 1.0 g of a gray solid, with a yield of 80.5%. LC-MS (APCI): m/z=261.1 (M−1$^-$). $^1$H NMR (300 MHz, CDCl$_3$) δ (ppm): 5.80 (d, J=6.4 Hz, 1H), 4.23-4.20 (m, 1H), 4.05-4.01 (m, 2H), 3.68 (s, 1H), 3.60-3.54 (m, 2H), 2.06-2.02 (m, 2H), 1.67-1.59 (m, 2H).

Step 4 Synthesis of Compound 29

Compound 27 (1.0 g, 3.82 mmol) and MeOD (30 mL) were added into a 100 mL single-necked flask equipped with a magnetic stirrer, and stirred at room temperature under nitrogen for 3 hours. Pd/C (100 mg, 10%) was added, and the resulting mixture was vacuumed and purged with deuterium gas for three times, and stirred and reacted at room temperature under a deuterium balloon for 2 hours. Dichloromethane (50 mL) was added, and the catalyst was filtered off. The catalyst was washed with dichloromethane (5 mL), and the filtrate was concentrated under reduced pressure, and purified by silica gel column chromatography to give 0.8 g of a white solid, with a yield of 79.5%. LC-MS (APCI): m/z=270.2 (M−1)$^-$. $^1$H NMR (500 MHz, CDCl$_3$) δ (ppm): 5.00 (d, J=7.0 Hz, 1H), 4.25-4.22 (m, 1H), 4.05-4.01 (m, 2H), 3.60-3.54 (m, 2H), 2.06-2.02 (m, 2H), 1.60-1.55 (m, 2H).

Step 5 Synthesis of Compound 30

Acetonitrile (20 mL) and compound 9 (1.74 g, 10 mmol) were added into a 50 mL single-necked flask equipped with a magnetic stirrer and a condenser. The resulting mixture was stirred to form a solution, after which compound 3 (2.2 g, 12 mmol) and potassium carbonate (2.1 g, 15 mmol) were added under stirring. The mixture was heated to 60° C. under nitrogen, stirred and reacted for 2 hours at this temperature. After cooling to room temperature, the solvent was evaporated under reduced pressure. Water (60 mL) was added, and a large amount of yellow solid was precipitated out. After the filtration, the residue was washed with water (20 mL), and dried to give 2.6 g of a yellow solid, with a yield of 77.1%. LC-MS (APCI): m/z=335.2 (M+1)$^+$.

Step 6 Synthesis of Compound 31

Compound 30 (1.34 g, 4.0 mmol) and methanol (20 mL) were added into a 50 mL single-necked flask equipped with a magnetic stirrer, and stirred to form a solution. Pd/C (0.14 g, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 1.18 g of a light brown solid, with a yield of 98.2%. LC-MS (APCI): m/z=305.2 (M+1)$^+$.

Step 7 Synthesis of Compound 32

Compound 29 (100 mg, 0.37 mmol), compound 31 (347 mg, 1.11 mmol), Pd(OAc)$_2$ (palladium acetate, 25 mg, 0.11 mmol), BINAP (2,2'-bis(diphenylphosphino)-1,1'-binaphthalene, 69 mg, 0.11 mmol) and cesium carbonate (481 mg, 1.48 mmol) were added into a 50 mL double-necked flask equipped with a magnetic stirrer. The resulting mixture was vacuumed and purged with nitrogen for three times, and anhydrous 1,4-dioxane (10 mL) was added through syringe. The resulting mixture was heated to 120° C., stirred and reacted for 4 hours at this temperature. After cooling to room temperature, dichloromethane (40 mL) was added, and the insoluble solid was filtered off. The filtrate was concentrated and purified by silica gel column chromatography to give 120 mg of a white powder, with a yield of 60.3%. LC-MS (APCI): m/z=540.4 (M+1)$^+$. $^1$H NMR (400 MHz, CDCl$_3$) δ (ppm): 7.21 (dd, J=8.4 Hz, J=2.0 Hz, 1H), 6.87-6.84 (m, 2H), 6.69 (s, 1H), 4.75 (d, J=7.2 Hz, 1H), 4.1-4.08 (m, 1H), 4.02-3.99 (m, 2H), 3.88 (s, 3H), 3.56-3.45 (m, 4H), 2.90-2.47 (m, 11H), 2.41 (s, 3H), 2.05-1.95 (m, 4H), 1.87-1.79 (m, 2H), 1.60-1.51 (m, 2H).

Step 8 Synthesis of Compound T-4

Compound 32 (120 mg, 0.22 mmol) and MeOD (8 mL) were added into a 50 mL double-necked flask equipped with a magnetic stirrer. Then anhydrous DMSO (2 mL) was added under stirring, and stirred to form a solution. Hydrogen peroxide (1 mL, 33%) was slowly added dropwise, after which, the resulting mixture was stirred and reacted at room temperature under nitrogen for half an hour. Acetonitrile (8 mL) was added, and stirred for 5 minutes. Water (40 mL) and ethyl acetate (40 mL) were added, and the resulting mixture was allowed to stand for the separation of layers. The organic phase was separated, and the aqueous phase was extracted with ethyl acetate (40 mL×2). The organic phases were combined, washed with water (60 mL×2) and saturated brine (30 mL), and dried over anhydrous sodium sulfate. After the filtration and concentration, the residue was purified by silica gel column chromatography to give 100 mg of a yellow solid, with a yield of 81.6%. LC-MS (APCI): m/z=558.4 (M+1)$^+$. $^1$H NMR (500 MHz, CDCl$_3$) δ (ppm): 10.73 (s, 1H), 7.51 (br s, 1H), 7.46 (dd, J=9.0 Hz, J=2.5 Hz, 1H), 6.91 (d, J=2.5 Hz, 1H), 6.84 (d, J=9.0 Hz, 1H), 5.21 (br s, 1H), 4.62 (d, J=7.0 Hz, 1H), 4.22-4.19 (m, 1H), 4.04-4.01 (m, 2H), 3.87 (s, 3H), 3.57-3.51 (m, 4H), 2.82-2.48 (m, 11H), 2.39 (s, 3H), 2.10-2.07 (m, 2H), 1.96-1.94 (m, 2H), 1.87-1.80 (m, 2H), 1.61-1.53 (m, 2H).

Example 5 Preparation of 6-(ethyl-$d_5$)-3-((3-methoxy-4-(4-(4-(methyl-$d_3$)piperazin-1-yl)piperidin-1-yl)phenyl)amino)-5-(((tetrahydro-2H-pyran-4-yl)amino)pyrazine-2-carboxamide (Compound T-5)

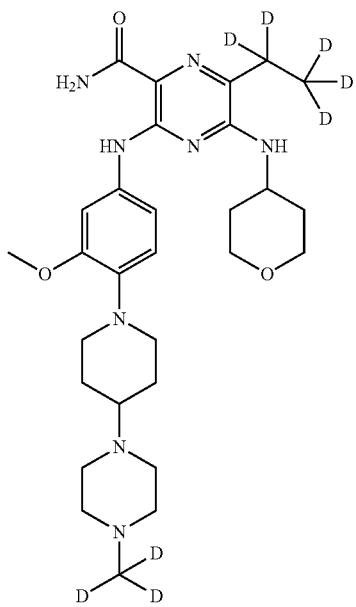

The following route was used for the synthesis:

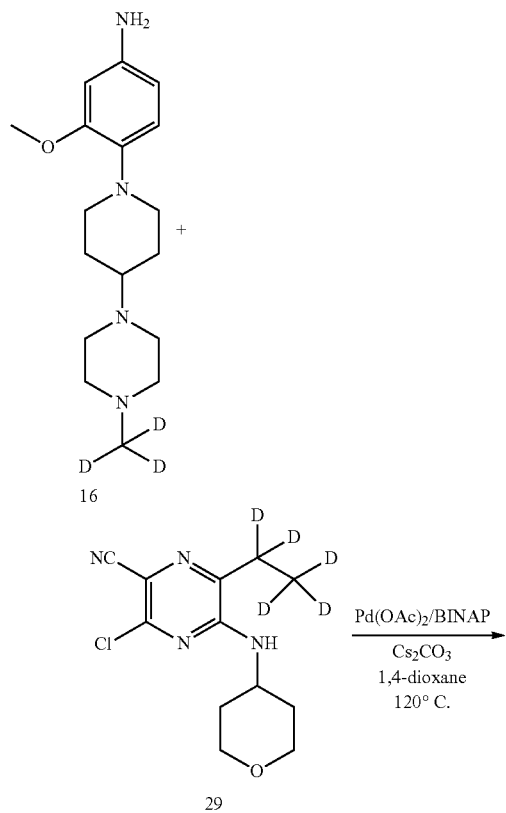

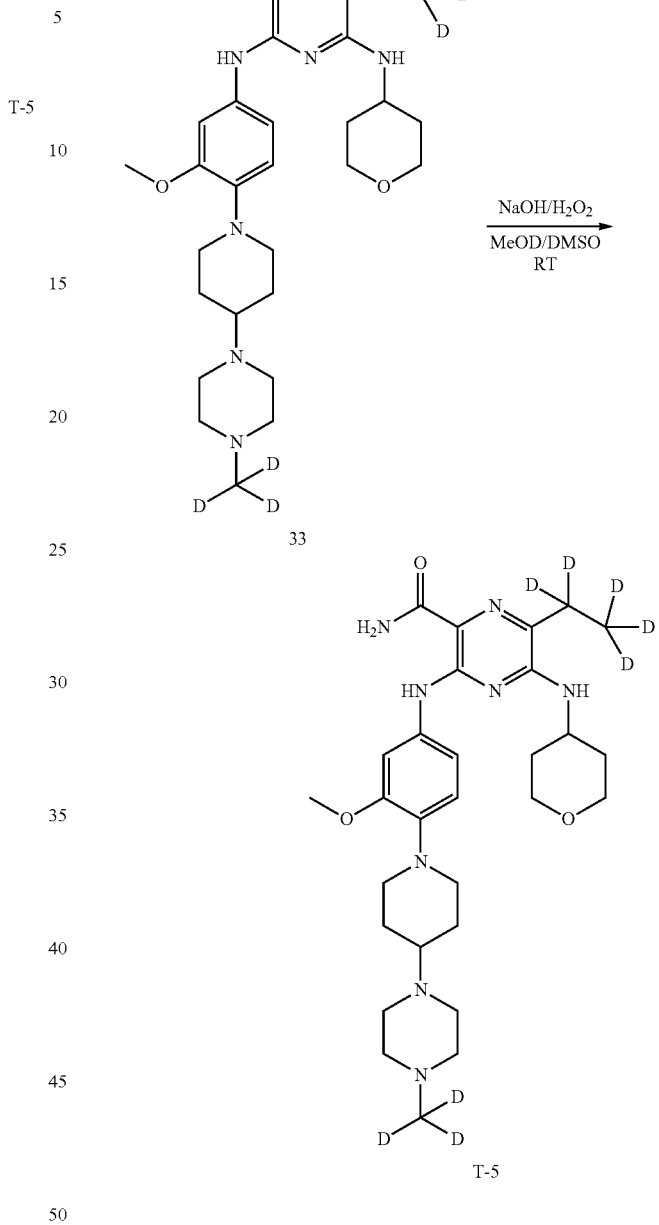

Step 1 Synthesis of Compound 33

Compound 29 (100 mg, 0.37 mmol), compound 16 (347 mg, 1.11 mmol), Pd(OAc)$_2$ (25 mg, 0.11 mmol), BINAP (69 mg, 0.11 mmol) and cesium carbonate (481 mg, 1.48 mmol) were added into a 50 mL double-necked flask equipped with a magnetic stirrer. The resulting mixture was vacuumed and purged with nitrogen for three times, and anhydrous 1,4-dioxane (10 mL) was added through syringe. The resulting mixture was heated to 120° C., stirred and reacted for 4 hours at this temperature. After cooling to room temperature, dichloromethane (40 mL) was added, and the insoluble solid was filtered off. The filtrate was concentrated and purified by silica gel column chromatography to give 120 mg of a white powder, with a yield of 60.3%. LC-MS (APCI): m/z=543.4 (M+1)$^+$. $^1$H NMR (400 MHz, CDCl$_3$) δ (ppm): 7.21 (dd, J=8.4 Hz, J=2.0 Hz, 1H), 6.87-6.84 (m, 2H), 6.69 (s, 1H), 4.75 (d, J=7.2 Hz, 1H), 4.1-4.08 (m, 1H), 4.02-3.99 (m, 2H), 3.88 (s, 3H), 3.56-3.45 (m, 4H), 2.90-2.47 (m, 11H), 2.05-1.95 (m, 4H), 1.87-1.79 (m, 2H), 1.60-1.51 (m, 2H).

Step 2 Synthesis of Compound T-5

Compound 33 (120 mg, 0.22 mmol) and MeOD (8 mL) were added into a 50 mL double-necked flask equipped with a magnetic stirrer. Then anhydrous DMSO (2 mL) was added under stirring, and stirred to form a solution. Hydrogen peroxide (1 mL, 33%) was slowly added dropwise, after which, the resulting mixture was stirred and reacted at room temperature under nitrogen for half an hour. Acetonitrile (8 mL) was added, and stirred for 5 minutes. Water (40 mL) and ethyl acetate (40 mL) were added, and the resulting mixture was allowed to stand for the separation of layers. The organic phase was separated, and the aqueous phase was extracted with ethyl acetate (40 mL×2). The organic phases were combined, washed with water (60 mL×2) and saturated brine (30 mL), and dried over anhydrous sodium sulfate. After the filtration and concentration, the residue was purified by silica gel column chromatography to give 100 mg of a yellow solid, with a yield of 81.6%. LC-MS (APCI): m/z=561.4 (M+1)$^+$. $^1$H NMR (400 MHz, CDCl3) δ (ppm): 10.73 (s, 1H), 7.51 (br s, 1H), 7.46 (dd, J=8.8 Hz, J=2.5 Hz, 1H), 6.91 (d, J=2.4 Hz, 1H), 6.84 (d, J=8.8 Hz, 1H), 5.21 (br s, 1H), 4.62 (d, J=7.2 Hz, 1H), 4.22-4.19 (m, 1H), 4.04-4.01 (m, 2H), 3.87 (s, 3H), 3.57-3.51 (m, 4H), 2.82-2.48 (m, 11H), 2.10-2.07 (m, 2H), 1.96-1.94 (m, 2H), 1.87-1.80 (m, 2H), 1.61-1.53 (m, 2H).

Example 6 Preparation of 6-(ethyl-d$_5$)-3-((3-(methoxy-d$_3$)-4-(4-(4-methylpiperazin-1-yl)piperidin-1-yl)phenyl)amino)-5-(((tetrahydro-2H-pyran-4-yl)amino)pyrazine-2-carboxamide (Compound T-6)

The following route was used for the synthesis:

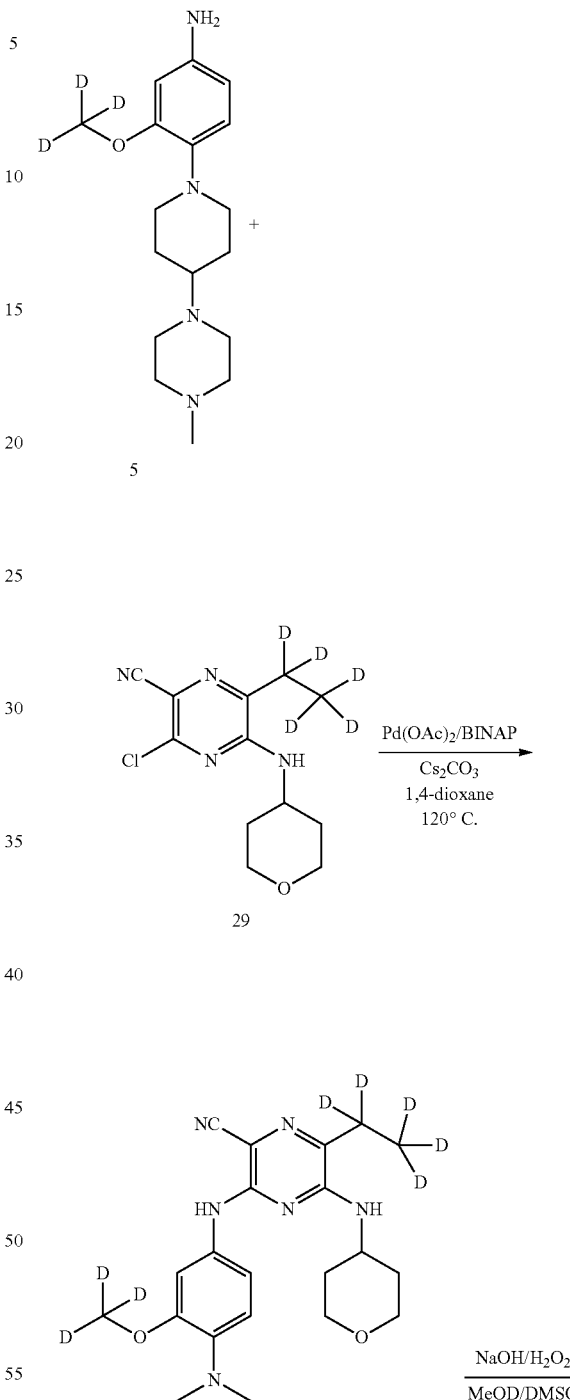

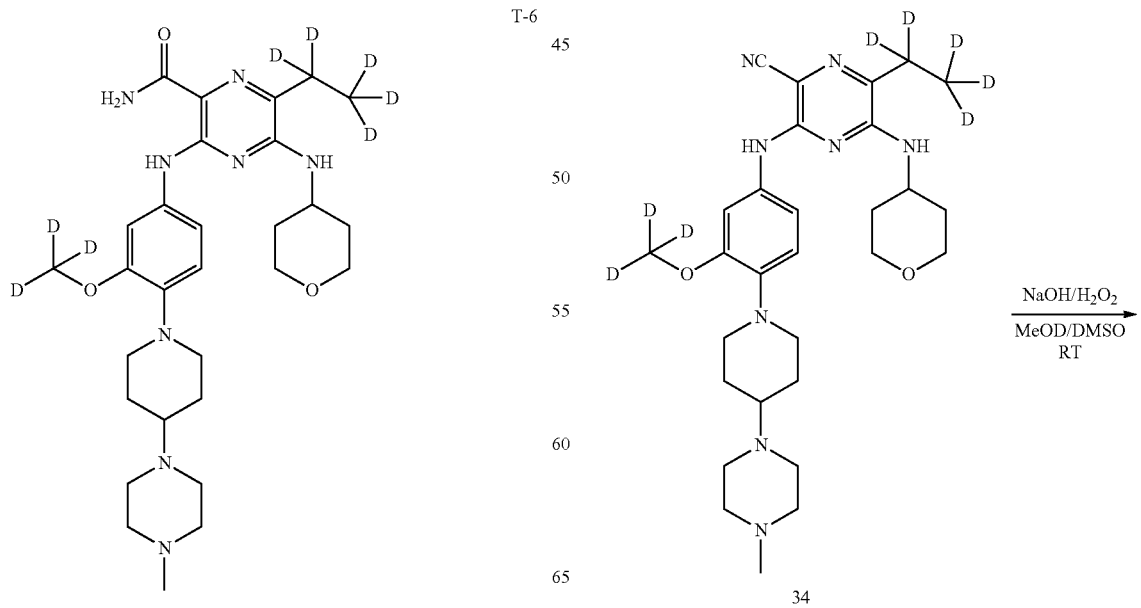

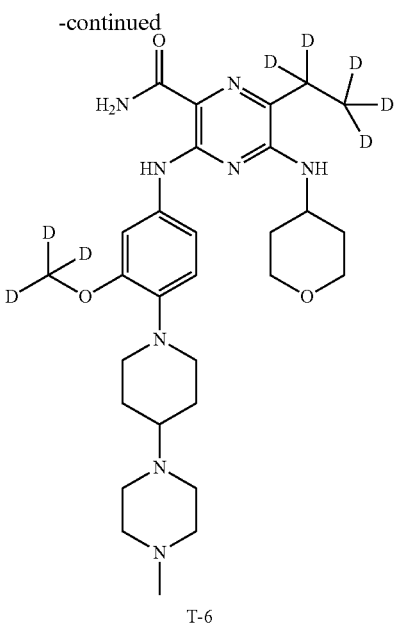

T-6

Step 1 Synthesis of Compound 34

Compound 29 (100 mg, 0.37 mmol), compound 5 (347 mg, 1.11 mmol), Pd(OAc)$_2$ (25 mg, 0.11 mmol), BINAP (69 mg, 0.11 mmol) and cesium carbonate (481 mg, 1.48 mmol) were added into a 50 mL double-necked flask equipped with a magnetic stirrer. The resulting mixture was vacuumed and purged with nitrogen for three times, and anhydrous 1,4-dioxane (10 mL) was added through syringe. The resulting mixture was heated to 120° C., stirred and reacted for 4 hours at this temperature. After cooling to room temperature, dichloromethane (40 mL) was added, and the insoluble solid was filtered off. The filtrate was concentrated and purified by silica gel column chromatography to give 120 mg of a white powder, with a yield of 60.3%. LC-MS (APCI): m/z=543.4 (M+1)$^+$. $^1$H NMR (400 MHz, CDCl$_3$) δ (ppm): 7.21 (dd, J=8.4 Hz, J=2.0 Hz, 1H), 6.87-6.84 (m, 2H), 6.69 (s, 1H), 4.75 (d, J=7.2 Hz, 1H), 4.1-4.08 (m, 1H), 4.02-3.99 (m, 2H), 3.56-3.45 (m, 4H), 2.90-2.47 (m, 11H), 2.41 (s, 3H), 2.05-1.95 (m, 4H), 1.87-1.79 (m, 2H), 1.60-1.51 (m, 2H).

Step 2 Synthesis of Compound T-6

Compound 34 (120 mg, 0.22 mmol) and MeOD (8 mL) were added into a 50 mL double-necked flask equipped with a magnetic stirrer. Then anhydrous DMSO (2 mL) was added under stirring, and stirred to form a solution. Hydrogen peroxide (1 mL, 33%) was slowly added dropwise, after which, the resulting mixture was stirred and reacted at room temperature under nitrogen for half an hour. Acetonitrile (8 mL) was added, and stirred for 5 minutes. Water (40 mL) and ethyl acetate (40 mL) were added, and the resulting mixture was allowed to stand for the separation of layers. The organic phase was separated, and the aqueous phase was extracted with ethyl acetate (40 mL×2). The organic phases were combined, washed with water (60 mL×2) and saturated brine (30 mL), and dried over anhydrous sodium sulfate. After the filtration and concentration, the residue was purified by silica gel column chromatography to give 100 mg of a yellow solid, with a yield of 81.6%. LC-MS (APCI): m/z=561.4 (M+1)$^+$. $^1$H NMR (400 MHz, CDCl3) δ (ppm): 10.73 (s, 1H), 7.51 (br s, 1H), 7.46 (dd, J=8.8 Hz, J=2.5 Hz, 1H), 6.91 (d, J=2.4 Hz, 1H), 6.84 (d, J=8.8 Hz, 1H), 5.21 (br s, 1H), 4.62 (d, J=7.2 Hz, 1H), 4.22-4.19 (m, 1H), 4.04-4.01 (m, 2H), 3.57-3.51 (m, 4H), 2.82-2.48 (m, 11H), 2.39 (s, 3H), 2.10-2.07 (m, 2H), 1.96-1.94 (m, 2H), 1.87-1.80 (m, 2H), 1.61-1.53 (m, 2H).

Example 7 Preparation of 6-ethyl-3-((3-methoxy-4-(4-(4-methylpiperazin-1-yl)piperidin-1-yl-3,3,5,5-d$_4$)phenyl)amino)-5-((tetrahydro-2H-pyran-4-yl)amino)pyrazine-2-carboxamide (Compound T-7)

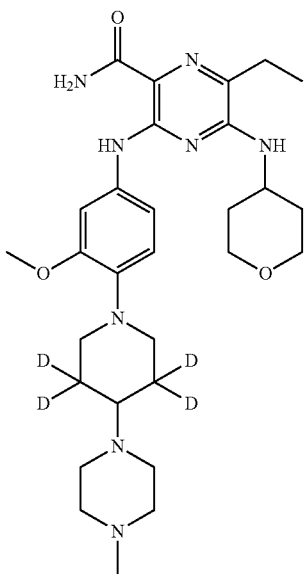

T-7

The following route was used for the synthesis:

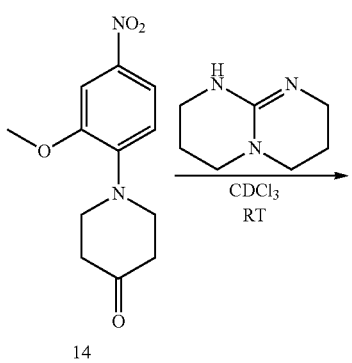

-continued
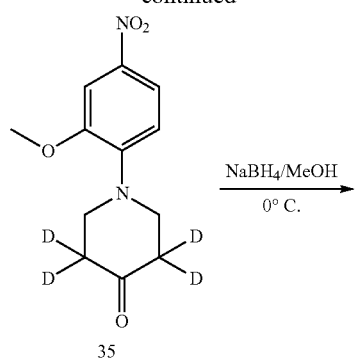
NaBH4/MeOH
0° C.
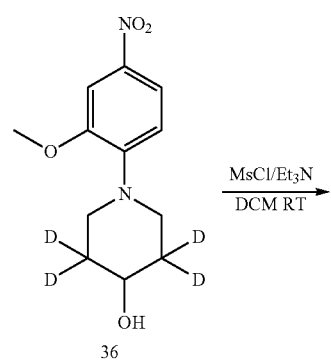
MsCl/Et3N
DCM RT
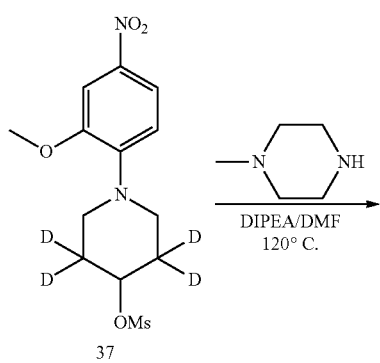
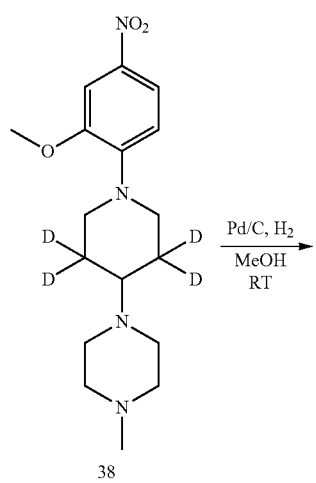
Pd/C, H2
MeOH
RT
-continued
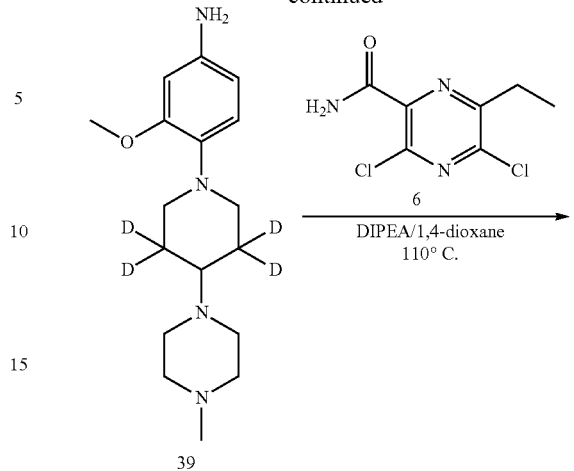
DIPEA/1,4-dioxane
110° C.
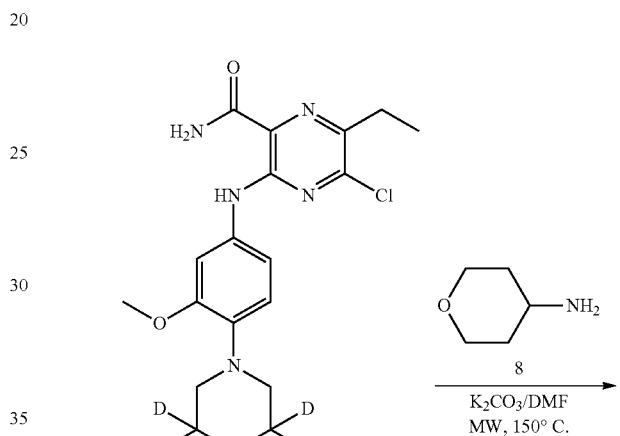
K2CO3/DMF
MW, 150° C.
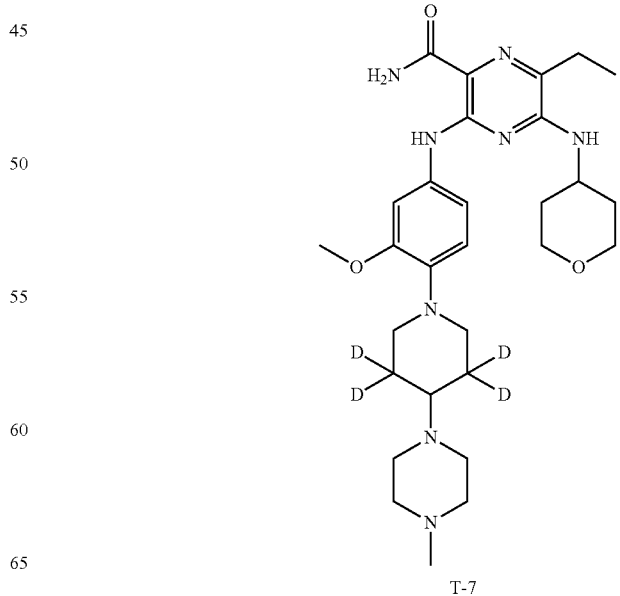

Step 1 Synthesis of Compound 35

Compound 14 (1.0 g, 4 mmol) and deuterated chloroform (80 mL) were added into a 250 mL single-necked flask equipped with a magnetic stirrer, and stirred to form a solution. 1,5,7-Triazabicyclo[4.4.0]dec-5-ene (75 mg, 0.55 mmol) was added under stirring, and the resulting mixture was stirred and reacted overnight at room temperature under nitrogen. The mixture was sequentially washed with water (20 mL) and 0.5 M hydrochloric acid (10 mL). The organic phase was dried over anhydrous sodium sulfate, filtered and concentrated to dryness to give 0.98 g of a yellow solid, with a yield of 98%. LC-MS (APCI): m/z=255.2 (M+1)$^+$.

Step 2 Synthesis of Compound 36

Methanol (20 mL) was added into a 100 mL single-necked flask equipped with a magnetic stirrer, and cooled to 0° C. Compound 35 (0.98 g, 4 mmol) was added, and stirred to form a solution. Sodium borohydride (168 mg, 4 mmol) was slowly added, and the resulting mixture was stirred and reacted for 5 minutes under nitrogen. Water (5 mL) was added to quench the reaction, and stirred at room temperature for 30 min. Water (60 mL) and ethyl acetate (60 mL) were sequentially added, and the organic phase was separated out. The aqueous phase was extracted with ethyl acetate (30 mL×2) and concentrated. The residue was dissolved in ethyl acetate (50 mL) again, and washed with saturated brine (20 mL×1). The organic phases were dried over anhydrous sodium sulfate, filtered and concentrated to give 0.99 g of a yellow solid, with a yield of 99%. LC-MS (APCI): m/z=257.2 (M+1)$^+$.

Step 3 Synthesis of Compound 37

Compound 36 (0.99 g, 4.0 mmol) and dichloromethane (20 mL) were added into a 50 mL single-necked flask equipped with a magnetic stirrer, and stirred to form a solution. Triethylamine (0.6 g, 6.0 mmol) was added, and methanesulfonyl chloride (0.57 g, 5.0 mmol) was slowly added dropwise. The resulting mixture was stirred and reacted at room temperature under nitrogen for 1 h. Water (30 mL) was added, shaked and the organic phase was separated out. The aqueous phase was extracted with dichloromethane (20 mL×2). The organic phases were combined, and washed sequentially with 0.5 M aqueous solution of hydrochloric acid (20 mL×1), saturated aqueous solution of sodium bicarbonate (15 mL×1), and saturated brine (15 mL×1). The resulting mixture was dried over anhydrous sodium sulfate, filtered and concentrated to give 1.2 g of a yellow solid, with a yield of 89.8%, which was used directly in the next step.

Step 4 Synthesis of Compound 38

Compound 37 (1.2 g, 3.6 mmol) and DMF (3 mL) were added into a 50 mL single-necked flask equipped with a magnetic stirrer, and stirred to form a solution. DIPEA (2.33 g, 18 mmol) and 1-methylpiperazine (3.6 g, 36 mmol) were added, and the resulting mixture was heated to 120° C. under nitrogen, and reacted overnight at this temperature. After cooling to room temperature, the solvent was evaporated under reduced pressure, and the residue was purified by silica gel column chromatography to give 0.6 g of a yellow solid, with a yield of 49.3%. LC-MS (APCI): m/z=339.2 (M+1)$^+$.

Step 5 Synthesis of Compound 39

Compound 38 (0.6 g, 1.78 mmol) and methanol (10 mL) were added into a 50 mL single-necked flask equipped with a magnetic stirrer, and stirred to form a solution. Pd/C (60 mg, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 0.52 g of a light brown solid, with a yield of 95.4%. LC-MS (APCI): m/z=309.2 (M+1)$^+$.

Step 6 Synthesis of Compound 40

Compound 39 (0.52 g, 1.69 mmol) and 1,4-dioxane (10 mL) were added into a 50 mL single-necked flask equipped with a magnetic stirrer and a condenser. The resulting mixture was stirred to form a solution, after which compound 6 (0.44 g, 2.0 mmol) and DIPEA (0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.6 g of a yellow solid, with a yield of 72.3%. LC-MS (APCI): m/z=492.3 (M+1)$^+$.

Step 7 Synthesis of Compound T-7

Compound 40 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=557.3 (M+1)$^+$. $^1$H NMR (400 MHz, CDCl$_3$) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.57-3.51 (m, 4H), 3.15-2.75 (m, 8H), 2.62-2.49 (m, 7H), 2.10-1.98 (m, 2H), 1.62-1.60 (m, 2H), 1.34-1.29 (m, 3H).

Example 8 Preparation of 6-ethyl-3-((3-methoxy-4-(4-(4-methylpiperazin-1-yl-2,2,3,3,5,5,6,6-d₈)piperidin-1-yl)phenyl)amino)-5-(((tetrahydro-2H-pyran-4-yl)amino)pyrazine-2-carboxamide (Compound T-8)
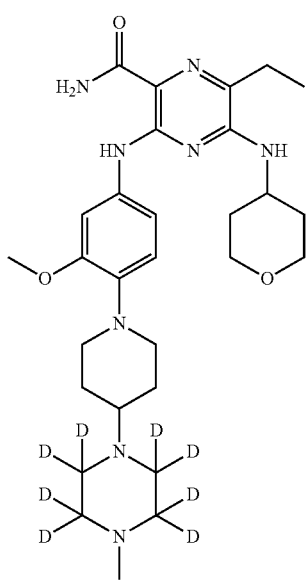
T-8
The following route was used for the synthesis:
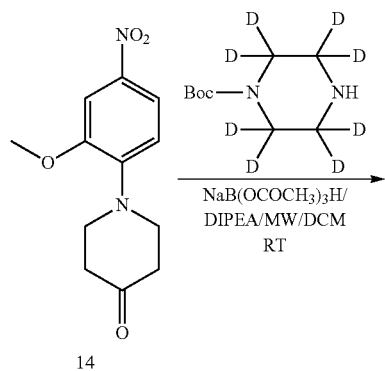
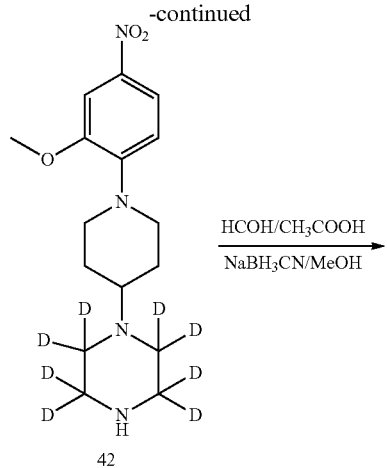
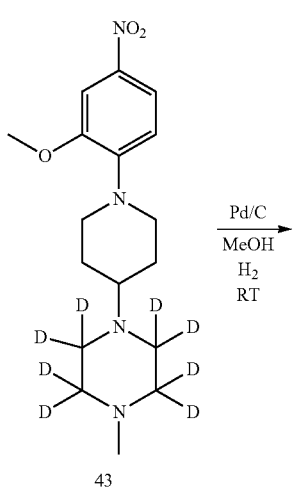
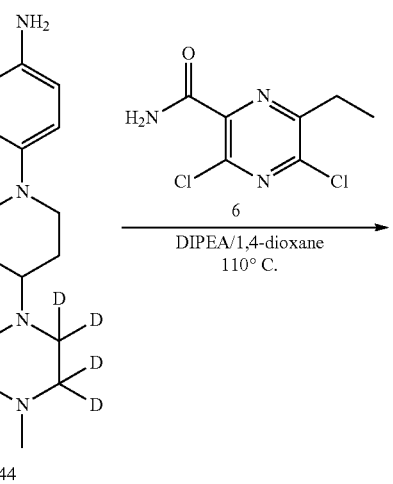

-continued

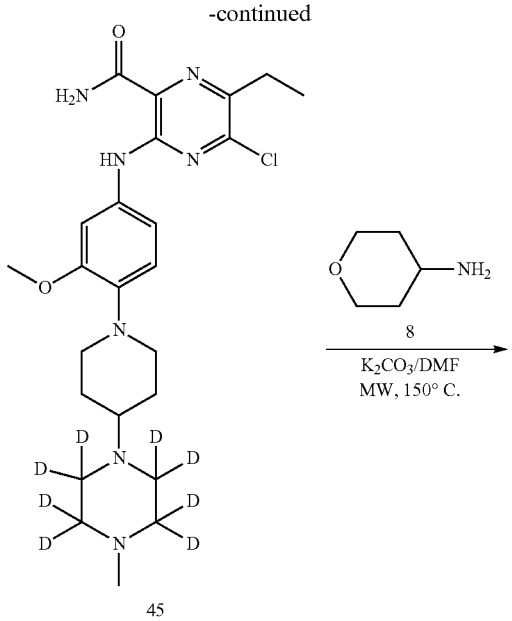

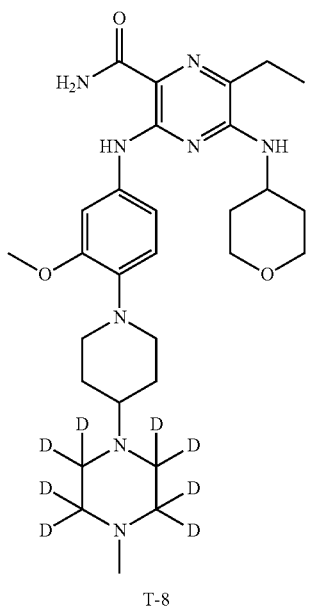

Step 1 Synthesis of Compound 41

Compound 14 (1.81 g, 7.2 mmol) and dichloromethane (18 mL) were added into a 50 mL single-necked flask equipped with a magnetic stirrer, and stirred to form a solution. N-Boc-piperazin-2,2,3,3,5,5,6,6-$d_8$ (1.8 g, 9.4 mol) and DIPEA (0.47 g, 3.6 mol) were sequentially added, and stirred for 10 minutes to form a solution. Powder 4 Å molecular sieve (1.44 g) was added, and stirred for 10 minutes. Sodium triacetoxyborohydride (3.05 g, 14.4 mol) was added in one portion, stirred and reacted overnight at room temperature under the protection of nitrogen. Water (40 mL) was added, and stirred for 20 minutes. Then the molecular sieve was filtered off through celite, after which the water phase was separated from the filtrate, and extracted with dichloromethane (30 mL×3). The organic phases were combined, and dried over anhydrous sodium sulfate. After the filtration and concentration, the residue was purified by silica gel column chromatography to give 2.2 g of a yellow solid, with a yield of 71.4%. LC-MS (APCI): m/z=429.2 (M+1)$^+$.

Step 2 Synthesis of Compound 42

Compound 41 (2.2 g, 5.14 mmol) and dichloromethane (20 mL) were added into a 50 mL single-necked flask equipped with a magnetic stirrer, and stirred to form a solution. Trifluoroacetic acid (10 mL) was added, and the resulting mixture was stirred for 2 hours at room temperature under nitrogen. The solvent was evaporated under reduced pressure, and dichloromethane (30 mL) was added. A solution of ammonia in methanol (7 M) was added dropwise under stirring, and the pH was adjusted to 10. After stirring for 10 minutes, the generated ammonium chloride solid was filtered off, and the filtrate was concentrated under reduced pressure to give 1.6 g of a yellow solid, with a yield of 94.9%. LC-MS (APCI): m/z=329.2 (M+1)$^+$.

Step 3 Synthesis of Compound 43

Compound 42 (1.0 g, 3.13 mmol) and MeOH (10 mL) were added into a 50 mL single-necked flask equipped with a magnetic stirrer, and stirred to form a solution. A solution of formaldehyde in water (0.56 g, 3.76 mmol, 20% w/w) and three drops of glacial acetic acid were added dropwise, stirred for 10 minutes under nitrogen. Sodium cyanoborohydride (0.31 g, 4.70 mmol) was added, and further stirred and reacted for 1 hour. Saturated aqueous solution of sodium bicarbonate (20 mL) was added to quench the reaction, and the resulting mixture was extracted with dichloromethane (30 mL×3). The organic phases were combined, washed with saturated brine (20 mL), and dried over anhydrous sodium sulfate. After the filtration and concentration, the residue was purified by silica gel column chromatography to give 0.85 g of a yellow solid, with a yield of 80.6%. LC-MS (APCI): m/z=343.2 (M+1)$^+$.

Step 4 Synthesis of Compound 44

Compound 43 (0.68 g, 2.0 mmol) and methanol (10 mL) were added into a 50 mL single-necked flask equipped with a magnetic stirrer, and stirred to form a solution. Pd/C (70 mg, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The filtrate was washed with dichloromethane (5 mL), and concentrated under reduced pressure to give 0.6 g of a light brown solid, with a yield of 98.2%. LC-MS (APCI): m/z=313.2 (M+1)$^+$.

Step 5 Synthesis of Compound 45

Compound 44 (0.6 g, 2.0 mmol) and 1,4-dioxane (10 mL) were added into a 50 mL single-necked flask equipped with a magnetic stirrer and a condenser. The resulting mixture was stirred to form a solution, after which compound 6 (0.50 g, 2.28 mmol) and DIPEA (0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.82 g of a yellow solid, with a yield of 83.7%. LC-MS (APCI): m/z=496.3 (M+1)⁺.

Step 6 Synthesis of Compound T-8

Compound 45 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=559.3 (M+1)⁺. ¹H NMR (400 MHz, CDCl₃) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.87 (s, 3H), 3.57-3.51 (m, 4H), 2.62-2.49 (m, 5H), 2.41 (s, 3H), 2.10-1.98 (m, 4H), 1.88-1.85 (m, 2H), 1.62-1.60 (m, 2H), 1.34-1.29 (m, 3H).

Example 9 Preparation of 6-ethyl-3-((3-methoxy-4-(4-(4-(methyl-d₃)piperazin-1-yl-2,2,3,3,5,5,6,6-d₈)piperidin-1-yl)phenyl)amino)-5-(((tetrahydro-2H-pyran-4-yl)amino)pyrazine-2-carboxamide (Compound T-9)

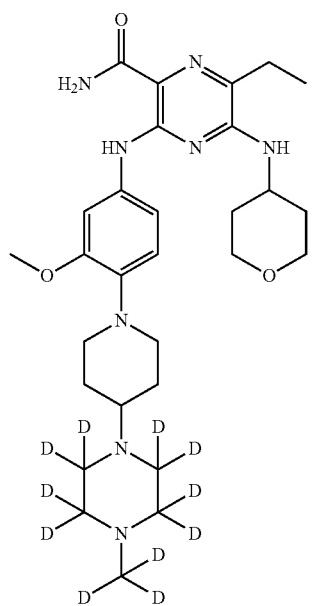

T-9

The following route was used for the synthesis:

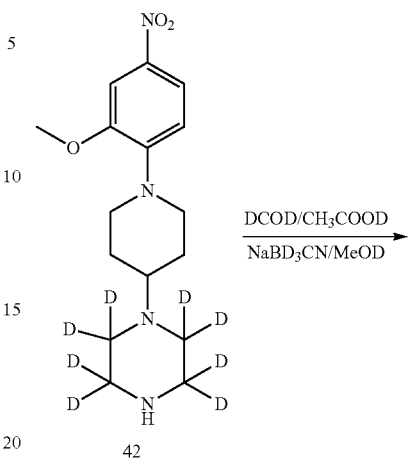

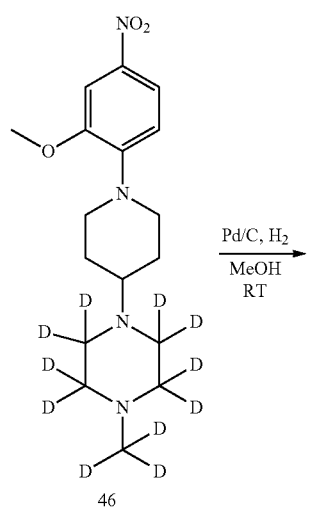

-continued

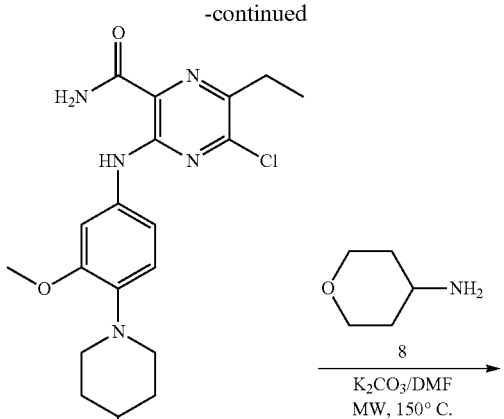

48

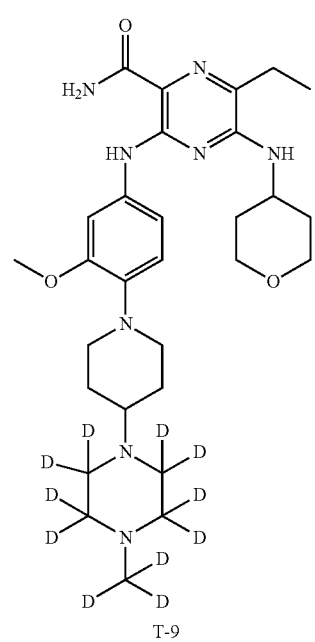

T-9

Step 1 Synthesis of Compound 46

Compound 42 (1.0 g, 3.13 mmol) and MeOD (10 mL) were added into a 50 mL single-necked flask equipped with a magnetic stirrer, and stirred to form a solution. A solution of deuterated formaldehyde in heavy water (0.56 g, 3.76 mmol, 20% w/w) and three drops of CH₃COOD were added dropwise, stirred for 10 minutes under nitrogen. Deuterated sodium cyanoborohydride (0.31 g, 4.70 mmol) was added, and further stirred and reacted for 1 hour. Saturated aqueous solution of sodium bicarbonate (20 mL) was added to quench the reaction, and the resulting mixture was extracted with dichloromethane (30 mL×3). The organic phases were combined, washed with saturated brine (20 mL), and dried over anhydrous sodium sulfate. After the filtration and concentration, the residue was purified by silica gel column chromatography to give 0.85 g of a yellow solid, with a yield of 80.6%. LC-MS (APCI): m/z=346.2 (M+1)$^+$.

Step 2 Synthesis of Compound 47

Compound 46 (0.68 g, 2.0 mmol) and methanol (10 mL) were added into a 50 mL single-necked flask equipped with a magnetic stirrer, and stirred to form a solution. Pd/C (70 mg, 10%) was added, and the resulting mixture was vacuumed and purged with hydrogen for three times, and stirred and reacted overnight at room temperature under a hydrogen balloon. Dichloromethane (30 mL) was added, and the catalyst was filtered off. The catalyst was washed with dichloromethane (5 mL), and the filtrate was concentrated under reduced pressure to give 0.6 g of a light brown solid, with a yield of 98.2%. LC-MS (APCI): m/z=316.2 (M+1)$^+$.

Step 3 Synthesis of Compound 48

Compound 47 (0.6 g, 2.0 mmol) and 1,4-dioxane (10 mL) were added into a 50 mL single-necked flask equipped with a magnetic stirrer and a condenser. The resulting mixture was stirred to form a solution, after which compound 6 (0.50 g, 2.28 mmol) and DIPEA (0.8 mL, 5.0 mmol) were added. The mixture was heated to 110° C. under nitrogen, stirred and reacted overnight at this temperature. The solvent was evaporated by concentrating under reduced pressure, and the residue was purified by silica gel column chromatography to give 0.82 g of a yellow solid, with a yield of 83.7%. LC-MS (APCI): m/z=499.3 (M+1)$^+$.

Step 4 Synthesis of Compound T-9

Compound 48 (0.20 g, 0.41 mmol) and DMF (5 mL) were added into a 10 mL microwave reaction tube. The resulting mixture was stirred to form a solution, after which compound 8 (0.41 g, 4.1 mmol) and potassium carbonate (0.18 g, 1.21 mmol) were added. The mixture was heated to 150° C. in a microwave reactor, and reacted for 2 hours at this temperature. The solvent was evaporated under reduced pressure, and the residue was purified by silica gel column chromatography to give 0.16 g of a yellow solid, with a yield of 70.3%. LC-MS (APCI): m/z=564.3 (M+1)$^+$. $^1$H NMR (400 MHz, CDCl₃) δ (ppm): 10.69 (s, 1H), 7.53-7.46 (m, 2H), 6.91 (d, J=2.4 Hz, 1H), 6.83 (d, J=8.8 Hz, 1H), 5.17 (br s, 1H), 4.62 (d, J=7.2 Hz, 1H), 4.29-4.15 (m, 1H), 4.14-4.01 (m, 2H), 3.87 (s, 3H), 3.57-3.51 (m, 4H), 2.62-2.49 (m, 5H), 2.10-1.98 (m, 4H), 1.88-1.85 (m, 2H), 1.62-1.60 (m, 2H), 1.34-1.29 (m, 3H).

Biological Activity Assay (1) Kinase Activity Evaluation

Reagents and Materials:

Enzyme AXL: Invitrogen-A31516, substrate ULight-poly GT peptide (PerkinElmer-TRF0100-M), antibody Eu-labeled anti-phos (PT66) (PerkinElmer-AD0069), ATP (Sigma, Cat. No. A7699-1G), DMSO (Sigma, Cat. No. D2650), 96-well plate (Corning, Cat. No. 3365), 384-well plate (Greiner, Cat. No. 784076).

Specific Experimental Protocol:

The inhibitory activity of the test compounds against AXL was determined by the LANCE Ultra TR-FRET method.

The test compounds were dissolved in DMSO, and subjected to a 3-fold serial gradient dilution for 10 times. AXL kinase was transferred with different concentrations of pre-diluted compounds to a 384-well test plate and mixed for 10 minutes, in duplicate. The substrate and ATP were added to initiate the reaction, and incubated at room temperature for 90 minutes. The final reaction concentrations in the system were: 3 nM AXL, 4.75 uM ATP, 50 nM peptide, 50 mM Hepes pH7.5, 1 mM EGTA, 10 mM $MgCl_2$, 0.01% Brij-35, and 2 mM DTT. The maximum concentration of the test compounds was 300 nM. After the reaction, the detection reagent containing 2 nM antibody and 10 mM EDTA was added and incubated at room temperature for 60 minutes. Finally, the enzyme activity in the presence of the compounds of the present disclosure at each concentration was measured by an Evnvision microplate reader, and the inhibition of the enzyme by the compounds at each concentration was calculated. The inhibitions of the enzyme activity by the compounds at different concentrations were then fitted using Graphpad 5.0 software according to the four-parameter equation, and the $IC_{50}$ values were calculated.

The compounds of the present disclosure were tested in the above kinase inhibition assay, which were found to have potent activity against AXL and better inhibitory effect than Gilteritinib. The results for the representative example compounds are summarized in Table 1 below.

TABLE 1

| Example compound | AXL $IC_{50}$ (nM) |
|---|---|
| Gilteritinib | 7.46 |
| T-1 | 7.35 |
| T-2 | 7.01 |
| T-3 | 6.62 |
| T-4 | 5.87 |
| T-5 | 5.33 |
| T-6 | 5.15 |
| T-7 | 6.24 |
| T-8 | 7.10 |
| T-9 | 6.50 |

(2) Inhibition of Cell MV-4-11 and Cell MOLM-13

Materials and Instruments:

Cell MV-4-11 (ATCC, Cat. No. CRL-9591), cell MOLM-13 (COBIOER, Cat. No. CBP60678), RPMI-1640 (GIBCO, Cat. No. A10491-01), penicillin-streptomycin (GIBCO, Cat. No. 15140-122), fetal bovine serum (GIBCO, Cat. No. 10099-141), phosphate buffer solution PBS (GIBCO, Cat. No. 10010-031), DMSO (Sigma, Cat. No. D8418-1L), CelltiterGlo Assay kit (CTG) (Promega, Cat. No. G7573), 96-well plate with transparent flat bottom and black walls (PerkinElmer, Cat. No. 6005680-50), plate shaker (QILIN-BEIER, Cat. No. B-9002), centrifuge (Eppendorf, Cat. No. 5804R), $CO_2$ incubator (Thermo Scientific, Cat. No. 371), microscope (OLYMPUS Cat. No. CKX41), multi-plate reader (PerkinElmer, Cat. No. EnVision).

Experimental Protocol:

(1) Cell Culture:

The cell culture medium of MV-4-11 was IMDM+10% FBS+1% PS, and the cell density did not exceed $1×10^6$/ml.

The cell culture medium of MOLM-13 was RPMI1640+ 20% FBS+1% PS, and the cell density did not exceed $1×10^6$/ml.

(2) Preparation of Cell Suspension a) The medium was collected from the culture bottle and centrifuged at 1000 rpm for 5 min.

b) The supernatant was discarded, and the cells were resuspended in medium containing 10% fetal bovine serum, and counted to prepare a cell suspension (cell viability was greater than 90%).

c) The cell suspension was added into a 96-well plate, with 100 d in each well, namely 5000 MV-4-11 cells/ well; 5000 MOLM-13 cells/well.

d) The cell plate was cultured overnight in a 37° C., 5% $CO_2$ incubator.

(3) Preparation of Compounds

Dilution of Compounds in DMSO:

a) MV-4-11 cells: The compounds were diluted with DMSO from 10 mM to 60 uM, and then subjected to a 3-fold serial gradient dilution in DMSO from 60 uM, resulting in 9 concentrations.

b) MOLM-13 cells: The compounds were diluted with DMSO from 10 mM to 200 uM, and then subjected to a 3-fold serial gradient dilution in DMSO from 200 uM, resulting in 9 concentrations.

c) Compound Taxol was diluted with DMSO from 10 mM to 200 uM, and then subjected to a 3-fold serial gradient dilution in DMSO from 200 uM, resulting in 9 concentrations.

(4) Treatment of Cells with Compounds (after the Overnight Incubation of the Cell Plate)

a) Each well was replenished with 99 μl of growth medium containing 10% FBS, and then 1 μl of the diluted compound was added to the well. The concentration of DMSO was 0.5%.

b) Concentrations of the tested compounds were: MV-4-11 cells: 300, 100, 33.3, 11.1, 3.7, 1.23, 0.41, 0.137, 0.046, 0 [nM].

MOLM-13 cells: 1000, 333.3, 111.1, 37.04, 12.35, 4.1, 1.37, 0.46, 0.15, 0 [nM].

c) Concentrations of control compound Taxol were: 1000, 333.3, 111.1, 37.04, 12.35, 4.12, 1.37, 0.46, 0.15, 0 [nM].

d) The cell plate was placed in the incubator for 72 hours.

(5) CTG Assay a) The test plate was placed at room temperature and equilibrated for 30 minutes, and 60 μl of the culture medium was discarded.

b) 60 μl of CTG reagent (CelltiterGlo kit) was added, and the plate was placed on a rapid plate shaker to shake for 2 min, and then let it stand at room temperature for 20 min.

c) Envision was used to read the values.

(6) Data Analysis $IC_{50}$ values were calculated using GraphPad Prism 6 software. The $IC_{50}$ (half inhibitory concentration) values of the compounds were obtained by the following non-linear fitting formula.

$$Y = Bottom + (Top - Bottom)/(1 + 10^{((Log\ IC50 - X) * HillSlope)})$$

X: Log value of the compound concentration

Y: Inhibition rate (% inhibition)

% inhibition (inhibition rate)=100*(value of the High Control-value of the test compound well)/ (value of the High Control-value of the Low Control)

The compounds of the present disclosure were tested in the above test experiments. The results show that, compared with gilteritinib, the compounds of the present disclosure have more potent activity on cell MV-4-11 and cell MOLM-13. The results of the in vitro proliferation inhibition of cancer cells by representative examples are summarized in Table 2 below.

TABLE 2

| Example compound | MV-4-11 $IC_{50}$ (nM) | MOLM-1 $IC_{50}$ (nM) |
|---|---|---|
| Gilteritinib | 2.23 | 14.27 |
| T-1 | 2.17 | 15.00 |
| T-2 | 2.35 | 14.31 |
| T-3 | 2.25 | 14.22 |
| T-4 | 1.92 | 12.98 |
| T-5 | 2.01 | 12.02 |
| T-6 | 2.07 | 11.91 |
| T-7 | 1.64 | 12.67 |
| T-8 | 2.17 | 14.80 |
| T-9 | 2.03 | 14.52 |

(3) Inhibition and Selectivity on Ba/F3 FLT3-ITD Cells

Cell lines were cultured under the condition of 37° C., 5% $CO_2$ and 95% humidity: cell line Ba/F3 parental (suspended, 3000 cells/well, medium was RPMI-1640+10% FBS+8 ng/ml IL-3), cell line Ba/F3 FLT3-ITD (suspended, 3000 cells/well, medium was RPMI-1640+10% FBS)

Reagents and materials: Fetal bovine serum (FBS, GBICO, Cat. No. 10099-141), CellTiter-Glo® Luminescent Cell Viability Assay (Promega, Cat. No. G7572), 96-well plate with transparent flat bottom and black walls (Corning®, Cat. No. 3603), control compound AC220 (Selleck, Cat. No. S1526).

Instruments: SpectraMax multi-label microplate reader, MD, 2104-0010A; $CO_2$ incubator, Thermo Scientific, Model 3100 Series; biosafety cabinet, Thermo Scientific, Model 1300 Series A2; inverted microscope, Olympus, CKX41SF; refrigerator, SIEMENS, KK25E76TI.

Experimental Protocol:

Cell Culture and Inoculation:
1. Cells in the logarithmic growth phase were harvested and counted using a platelet counter. The cell viability was determined by trypan blue exclusion method to ensure that the cell viability was greater than 90%;
2. The cell concentration was adjusted and 90 μL of the cell suspension was added into a 96-well plate respectively;
3. The cells in the 96-well plate were cultured overnight under the condition of 37° C., 5% $CO_2$ and 95% humidity.

Drug Dilution and Dosing:
1. The 10-fold drug solutions were prepared with a maximum concentration of 100 μM, which was diluted using a 3.16-fold serial gradient dilution, resulting in 9 concentrations. 10 μL of the drug solutions was added to each well of the 96-well plate inoculated with Ba/F3 parental cells; and each drug concentration was set in triplicate.
2. The 10-fold drug solutions were prepared with a maximum concentration of 10 μM, which was diluted using a 3.16-fold serial gradient dilution, resulting in 9 concentrations. 10 μL of the drug solutions was added to each well of the 96-well plate inoculated with Ba/F3 FLT3-ITD cells; and each drug concentration was set in triplicate.
3. The cells in the 96-well plate with drugs were cultured at 37° C., 5% $CO_2$ and 95% humidity for 72 hours, and then CTG analysis was carried out.

Plate Reading at the End Point:
1. CTG reagent was thawed and the cell plate was equilibrated to room temperature for 30 minutes;
2. Equal volume of the CTG solution was added to each well;
3. The cell plate was shaked on the orbital shaker for 5 minutes to lyse the cells;
4. The cell plate was placed at room temperature for 20 minutes to stabilize the cold light signal;
5. The cold light values were read.

Data Processing

GraphPad Prism 8.0 software was used to analyze the data, and the data was fitted using the non-linear S-curve regression to get a dose-effect curve, and $IC_{50}$ values were calculated.

Cell viability (%)=(Lum of test drug−Lum of medium control)/(Lum of cell control−Lum of medium control)×100%.

The compounds of the present disclosure were tested in the above test experiments. The results show that the compounds of the present disclosure have potent activity on Ba/F3 FLT3-ITD and superior selectivity over cell Ba/F3 parental. The results of the in vitro inhibition of cell proliferation by the representative examples are summarized in Table 3 below.

TABLE 3

| Example compound | BaF3 parental $IC_{50}$ (nM) | BaF3 [FLT3-ITD] $IC_{50}$ (nM) | Selectivity |
|---|---|---|---|
| T-1 | 9715.14 | 46.45 | 209 |
| T-2 | 7160.09 | 51.30 | 140 |
| T-3 | 5368.11 | 89.04 | 60 |
| T-5 | 9294.25 | 94.41 | 98 |
| T-6 | >10000 | 69.09 | 145 |
| T-7 | 8432.19 | 53.88 | 156 |
| T-8 | 6870.09 | 84.99 | 81 |
| T-9 | >10000 | 72.04 | 139 |

(4) Metabolic Stability Evaluation

Microsome assay: human liver microsomes: 0.5 mg/mL, Xenotech; rat liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solutions: Powder of the example compounds and the control compound were accurately weighed and dissolved in DMSO to 5 mM respectively.

Preparation of phosphate buffer (100 mM, pH7.4): A pre-prepared 0.5 M potassium dihydrogen phosphate (150 mL) was mixed with 0.5 M dibasic potassium phosphate (700 mL). The pH of the mixture was adjusted to 7.4 with 0.5 M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL of human liver microsomes were added, and mixed to obtain a liver microsome dilution with a protein concentration of 0.625 mg/mL. 25057.5 μL of phosphate buffer (pH 7.4) was taken into a 50 mL centrifuge tube, to which 812.5 μL of SD rat microsomes were added, and mixed to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 μL of the dilutions of human liver microsomes and rat liver microsomes were added to 96-well incubation plates (N=2), respectively, and 2 μL of 0.25 mM working solution was added respectively and mixed.

Metabolic stability assay: 300 μL of pre-chilled stop solution was added to each well of 96-well deep well plates and placed on ice as stop plates. The 96-well incubation plates and NADPH regeneration system were placed in a 37° C. water bath, shaken at 100 rpm and pre-incubated for 5 min. 80 μL of incubation solution was taken out from each well of the incubation plates and added to the stop plates, mixed, and replenished with 20 μL of NADPH regeneration system solution as a 0-min sample. 80 μL of NADPH regeneration system solution was added to each well of the incubation plates to start the reaction and start counting. The corresponding compounds had a reaction concentration of 1 μM and the protein concentration was 0.5 mg/mL. Separately, 100 μL of the reaction solutions was taken at 10, 30, and 90 min after the reaction, respectively, added to stop plates, and vortexed for 3 minutes to terminate the reaction. The stop plates were centrifuged at 5000×g at 4° C. for 10 min. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of remaining compound versus time, and $t_{1/2}$ and $CL_{int}$ were calculated according to the equation below, where V/M equals to 1/protein concentration.

$$t_{1/2} = -\frac{0.693}{slope}, \quad CL_{int} = \frac{0.693}{t_{1/2}} \cdot \frac{V}{M},$$

$t_{1/2}$(min); $CL_{int}$(μL/min/mg).

The metabolic stability of the compounds in human and rat liver microsomes was evaluated by simultaneously testing and comparing the compounds disclosed herein and the non-deuterated compound. The non-deuterated compound Gilteritinib was used as a control sample. In the human and rat liver microsome assays, compared with the non-deuterated compound Gilteritinib, the compounds of the present disclosure can significantly improve the metabolic stability.

TABLE 4

| | Human liver microsome assay | |
|---|---|---|
| Compound No. | $t_{1/2}$ (min) | $CL_{int}$ (μL/min/mg) |
| Gilteritinib | 164.9 | 8.4 |
| T-2 | 217.6 | 6.4 |
| T-3 | 199.8 | 6.9 |
| T-5 | 188.3 | 7.4 |
| T-8 | 261.7 | 5.3 |
| T-9 | 472.6 | 2.9 |

(5) Pharmacokinetic Experiment in Rats

Six male Sprague-Dawley rats, 7 to 8 weeks old, weighing approximately 210 g, were divided into 2 groups with 3 rats in each group. The pharmacokinetic differences of the compounds were compared after they were administered to the rats at a single dose through vein (in vein 3 mg/kg) or mouth (orally 10 mg/kg).

The rats were fed with standard feed and water, and fasted 16 hours before the experiment. The drugs were dissolved with PEG400 and dimethyl sulfoxide. The blood samples were collected from eyelids at the time point of 0.083, 0.25, 0.5, 1, 2, 4, 6, 8, 12 and 24 hours after administration.

The rats were anesthetized for a short time after inhaling ether, and 300 μL of blood samples was collected from the eyelids and put into test tubes, which contains 30 μL of 1% heparin salt solution. The test tubes were dried overnight at 60° C. prior to use. After the blood sample collection at the last time point, the rats were sacrificed after the ether anesthesia.

Immediately after the collection of the blood samples, the test tubes were gently inverted at least 5 times to ensure the fully mixing and placed on ice. The blood samples were centrifuged at 4° C., 5000 rpm for 5 minutes to separate the plasma from the red blood cells. 100 μL of plasma was pipetted into a clean plastic centrifuge tube, with the name of the compound and time point on it. The plasma was stored at −80° C. before analysis, and LC-MS/MS was used to determine the concentration of the compounds disclosed herein in plasma. Pharmacokinetic parameters were calculated based on the plasma concentrations of each animal at different time points.

The experiment shows that the compounds disclosed herein have better pharmacokinetic properties in animals, and therefore have better pharmacodynamics and treatment effects. The results of the pharmacokinetic experiment in rats for the representative example compounds are summarized in Table 5 below.

TABLE 5

| | Gilteritinib | | T-1 | | T-4 | |
|---|---|---|---|---|---|---|
| PK Dose | IV 3 mg/kg | PO 10 mg/kg | IV 3 mg/kg | PO 10 mg/kg | IV 3 mg/kg | PO 10 mg/kg |
| $T_{max}$ (h) | 0.08 | 8.00 | 0.08 | 5.33 | 0.08 | 4.00 |
| $C_{max}$ (ng/mL) | 196.2 | 34.6 | 138.1 | 48.4 | 137.5 | 61.2 |
| $AUC_{last}$ (h * ng/mL) | 449.4 | 316.9 | 555.9 | 510.0 | 638.8 | 665.5 |
| $AUC_{INF\_pred}$ (h * ng/mL) | 508.7 | 435.2 | 572.0 | 578.2 | 651.3 | 686.6 |
| $MRT_{INF\_pred}$ (h) | 3.44 | 7.46 | 4.20 | 7.89 | 4.56 | 8.11 |
| $Vz_{\_pred}$ (L/kg) | 34.89 | 212.0 | 28.80 | 162.8 | 30.45 | 87.60 |
| $Cl_{\_pred}$ (L/kg) | 5.92 | 25.50 | 5.56 | 19.03 | 4.67 | 14.91 |
| $T_{1/2}$ (h) | 4.08 | 5.76 | 3.59 | 5.93 | 4.52 | 4.07 |
| F(%) | | 21.15 | | 27.52 | | 31.26 |

The invention claimed is:

1. A compound of Formula (II), or a pharmaceutically acceptable salt, prodrug, hydrate, solvate, polymorph, stereoisomer, or isotopic variant thereof:

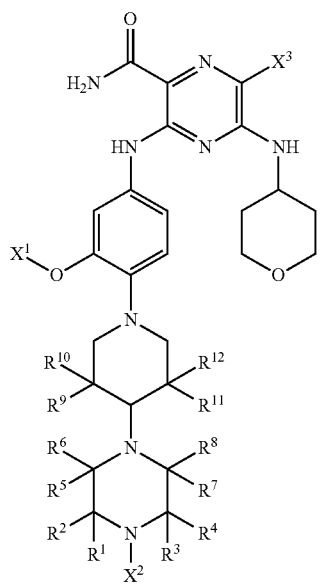

(II)

wherein
$R^1$, $R^2$, $R^3$, $R^4$, $R^5$, $R^6$, $R^7$, $R^8$, $R^9$, $R^{10}$, $R^{11}$ and $R^{12}$ are independently selected from hydrogen or deuterium;
$X^1$ and $X^2$ are independently selected from $CH_3$, $CD_3$, $CHD_2$ or $CH_2D$;
$X^3$ is selected from $CH_2CH_3$, $CH_2CH_2D$, $CH_2CHD_2$, $CH_2CD_3$, $CHDCH_3$, $CHDCH_2D$, $CHDCHD_2$, $CHDCD_3$, $CD_2CH_3$, $CD_2CH_2D$, $CD_2CHD_2$ or $CD_2CD_3$;
with the proviso that the compound contains at least one deuterium atom.

2. The compound according to claim 1, or the pharmaceutically acceptable salt, prodrug, hydrate, solvate, polymorph, stereoisomer, or isotopic variant thereof, wherein $R^9$, $R^{10}$, $R^{11}$ and $R^{12}$ are hydrogen.

3. The compound according to claim 1, or the pharmaceutically acceptable salt, prodrug, hydrate, solvate, polymorph, stereoisomer, or isotopic variant thereof, wherein $R^1$, $R^2$, $R^3$, $R^4$, $R^5$, $R^6$, $R^7$ and $R^8$ are hydrogen.

4. The compound according to claim 1, or the pharmaceutically acceptable salt, prodrug, hydrate, solvate, polymorph, stereoisomer, or isotopic variant thereof, wherein $X^2$ is $CD_3$.

5. The compound according to claim 1, or the pharmaceutically acceptable salt, prodrug, hydrate, solvate, polymorph, stereoisomer, or isotopic variant thereof, wherein $X^1$ is $CD_3$.

6. The compound according to claim 1, or the pharmaceutically acceptable salt, prodrug, hydrate, solvate, polymorph, stereoisomer, or isotopic variant thereof, wherein $X^3$ is $CD_2CD_3$.

7. The compound, or the pharmaceutically acceptable salt, prodrug, hydrate, solvate, polymorph, stereoisomer or isotopic variant thereof, according to claim 1, wherein the compound is selected from any one of the following compounds:

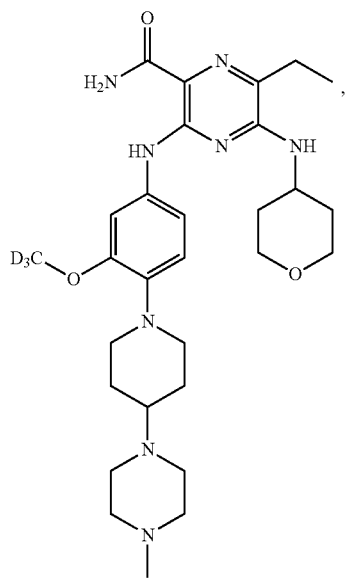

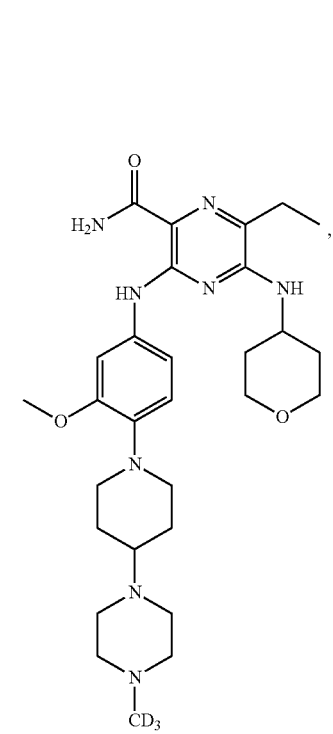

81
-continued
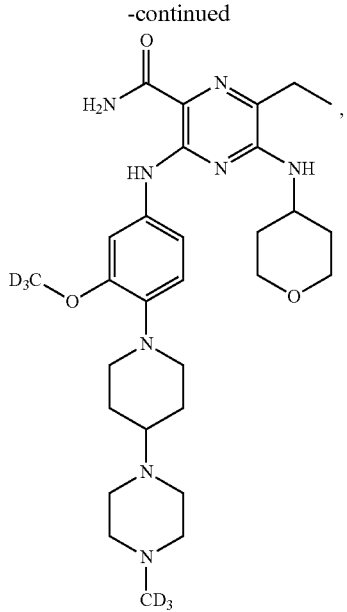
82
-continued
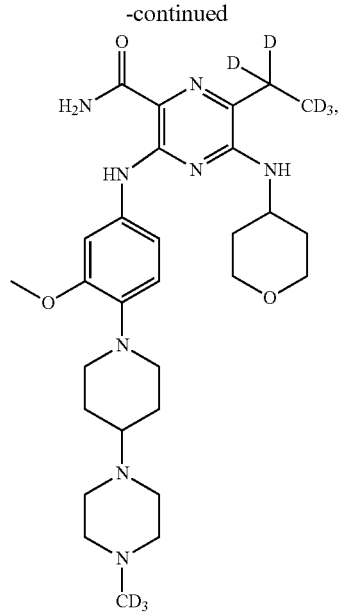
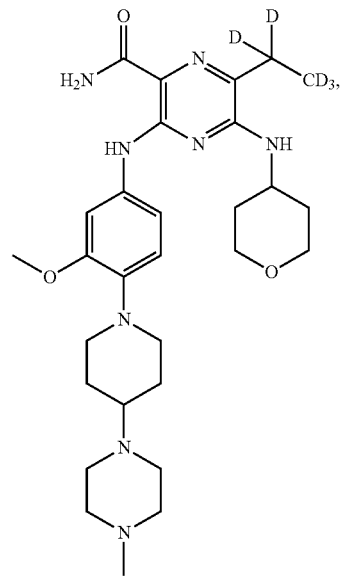
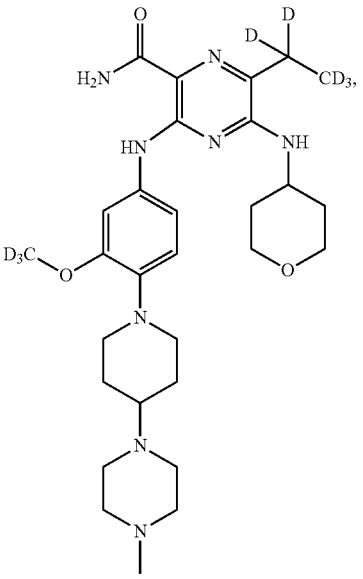

83
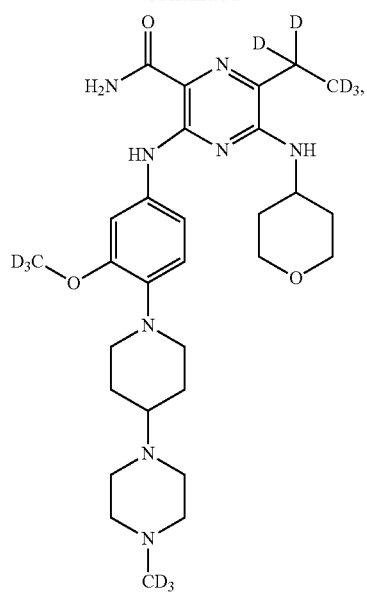
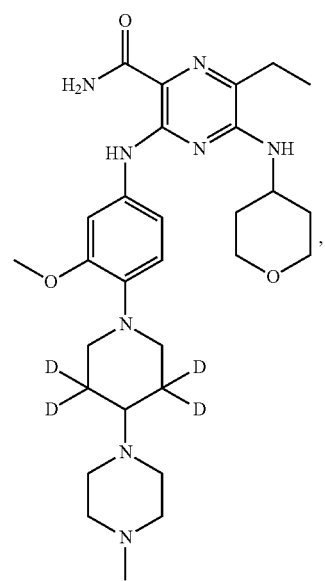
84
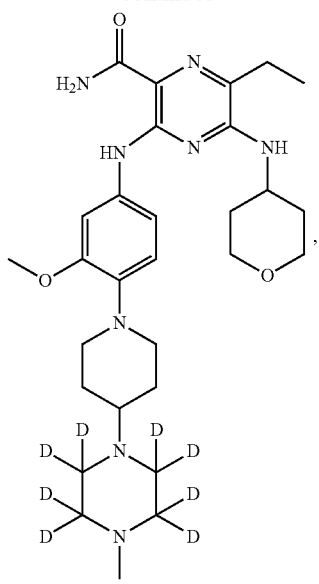
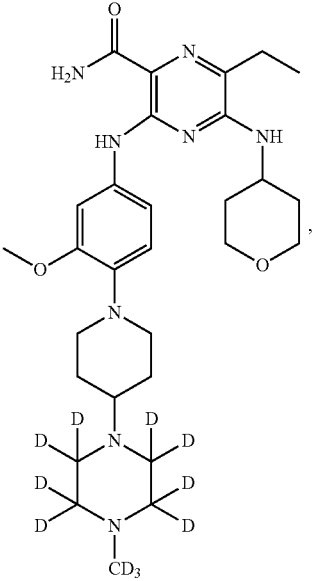

85
-continued
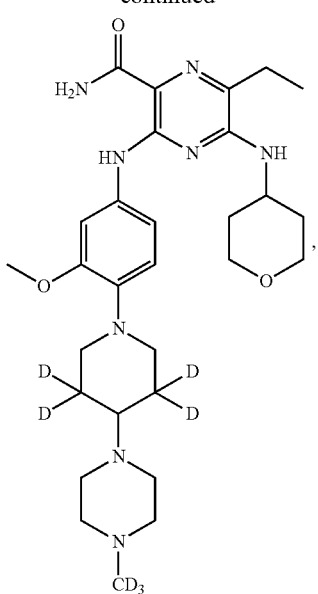
86
-continued
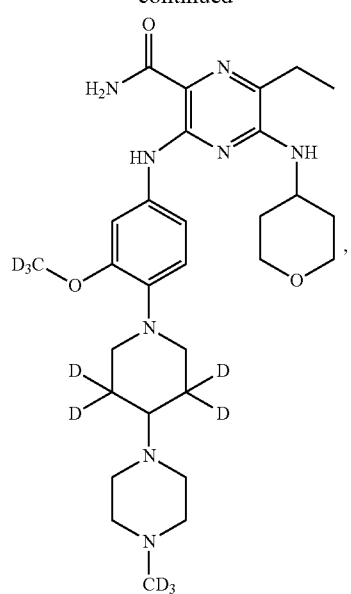
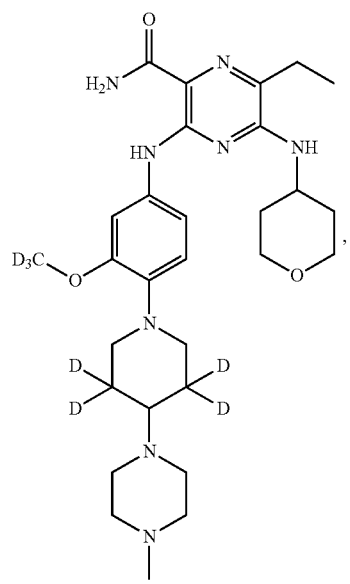
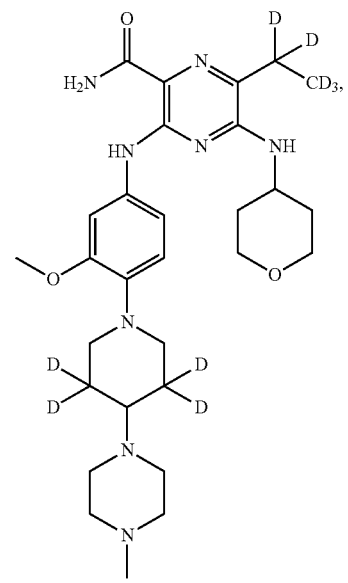

87
-continued
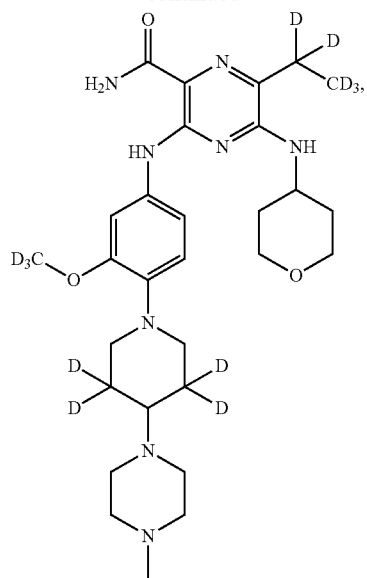
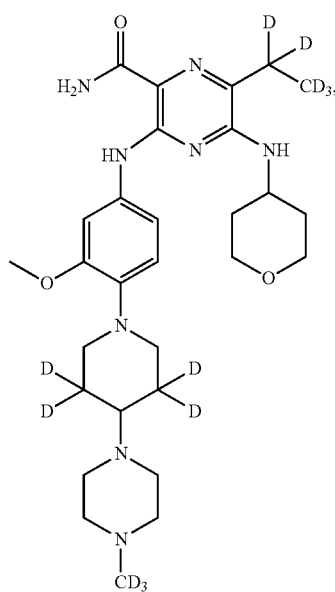
88
-continued
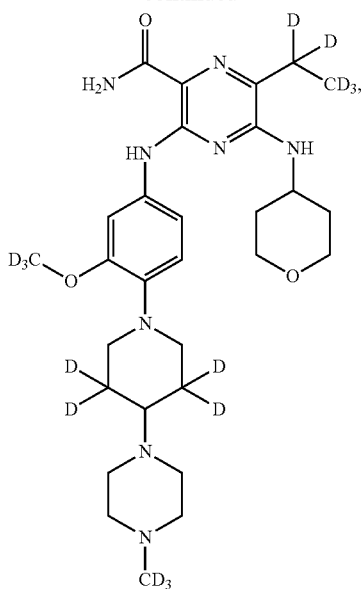
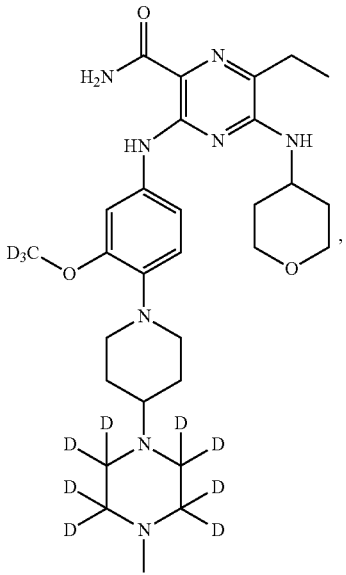

89
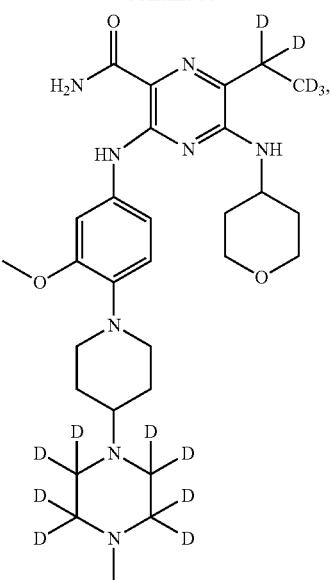
90
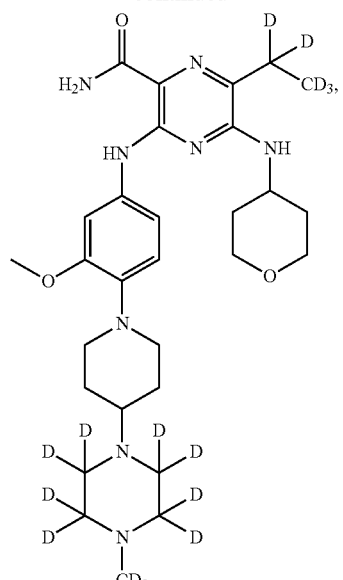
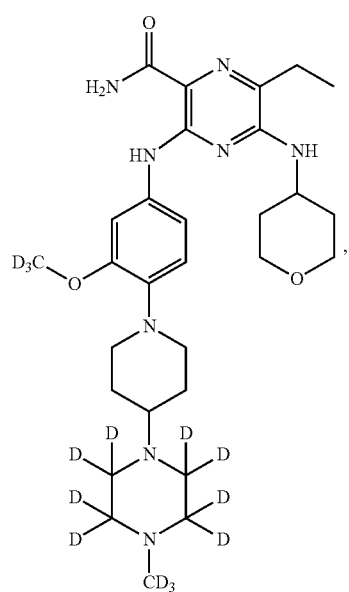
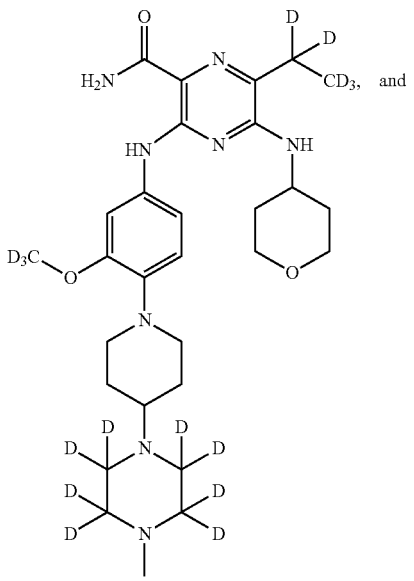

-continued

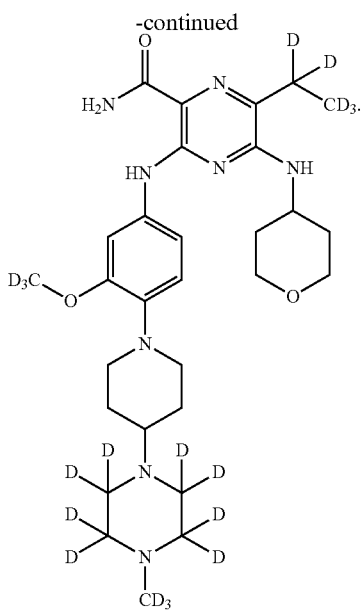

8. A pharmaceutical composition, comprising pharmaceutically acceptable excipient(s) and the compound, or the pharmaceutically acceptable salt, prodrug, hydrate, solvate, polymorph, stereoisomer, or isotopic variant thereof, according to claim 1.

9. A method of treating a FLT3 kinase-mediated disease in a subject, comprising administering an effective amount of the compound, or the pharmaceutically acceptable salt, prodrug, hydrate, solvate, polymorph, stereoisomer, or isotopic variant thereof, according to claim 1.

10. A method of treating an AXL kinase-mediated disease in a subject, comprising administering an effective amount of the compound, or the pharmaceutically acceptable salt, prodrug, hydrate, solvate, polymorph, stereoisomer, or isotopic variant thereof, according to claim 1.

11. A method of treating acute myeloid leukemia in a subject, comprising administering an effective amount of the compound, or the pharmaceutically acceptable salt, prodrug, hydrate, solvate, polymorph, stereoisomer, or isotopic variant thereof, according to claim 1.

12. A method of treating a FLT3 kinase-mediated disease in a subject, comprising administering the pharmaceutical composition according to claim 8.

13. A method of treating an AXL kinase-mediated disease in a subject, comprising administering the pharmaceutical composition according to claim 8.

* * * * *